United States Patent
Walker et al.

(10) Patent No.: US 10,745,376 B2
(45) Date of Patent: Aug. 18, 2020

(54) PROCESSES FOR THE PREPARATION OF HETEROARYL CARBOXYLIC ACIDS

(71) Applicant: Monsanto Technology LLC, St. Louis, MO (US)

(72) Inventors: Daniel Patrick Walker, Augusta, MO (US); William Harold Miller, Glendale, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/087,175

(22) PCT Filed: Mar. 21, 2017

(86) PCT No.: PCT/US2017/023322
§ 371 (c)(1),
(2) Date: Sep. 21, 2018

(87) PCT Pub. No.: WO2017/165356
PCT Pub. Date: Sep. 28, 2017

(65) Prior Publication Data
US 2019/0062299 A1  Feb. 28, 2019

Related U.S. Application Data

(60) Provisional application No. 62/423,357, filed on Nov. 17, 2016, provisional application No. 62/312,907, filed on Mar. 24, 2016.

(51) Int. Cl.
| | | |
|---|---|---|
| C07D 333/40 | (2006.01) |
| B01J 27/25 | (2006.01) |
| B01J 23/75 | (2006.01) |
| B01J 23/889 | (2006.01) |
| B01J 23/74 | (2006.01) |
| C07D 413/04 | (2006.01) |
| B01J 27/20 | (2006.01) |
| C07D 271/06 | (2006.01) |
| B01J 23/85 | (2006.01) |
| B01J 23/89 | (2006.01) |
| B01J 31/12 | (2006.01) |

(52) U.S. Cl.
CPC ............ C07D 333/40 (2013.01); B01J 23/74 (2013.01); B01J 23/75 (2013.01); B01J 23/8892 (2013.01); B01J 27/20 (2013.01); B01J 27/25 (2013.01); C07D 271/06 (2013.01); C07D 413/04 (2013.01); B01J 23/85 (2013.01); B01J 23/889 (2013.01); B01J 23/89 (2013.01); B01J 31/12 (2013.01)

(58) Field of Classification Search
CPC .................................................. C07D 333/40
See application file for complete search history.

(56) References Cited

U.S. PATENT DOCUMENTS

| | | | |
|---|---|---|---|
| 2,229,897 A | 1/1941 | Migrdichian | |
| 3,741,984 A | 6/1973 | Sheeran | |
| 3,959,569 A | 5/1976 | Burkholder, Jr. | |
| 4,556,672 A | 12/1985 | Kadin | |
| 5,312,914 A | 5/1994 | Sedelmeier et al. | |
| 5,534,541 A | 7/1996 | Drauz et al. | |
| 7,579,511 B1 | 8/2009 | Dakka et al. | |
| 7,659,411 B2 | 2/2010 | Bando et al. | |
| 8,435,999 B2 | 5/2013 | Williams et al. | |
| 9,040,711 B2 | 5/2015 | Miller et al. | |
| 9,273,037 B2 | 3/2016 | Miller et al. | |
| 10,239,857 B2 * | 3/2019 | Walker ................. | C07D 271/06 |
| 2007/0149787 A1 | 6/2007 | Bando et al. | |
| 2008/0167286 A1 | 10/2008 | Gopalakrishnan | |
| 2011/0112311 A1 | 5/2011 | Ando | |
| 2012/0302773 A1 | 11/2012 | Janka et al. | |
| 2014/0039197 A1 | 2/2014 | Miller et al. | |
| 2014/0171679 A1 | 6/2014 | Shih et al. | |
| 2014/0249300 A1 | 9/2014 | Bozell et al. | |
| 2015/0051412 A1 | 2/2015 | Janka et al. | |

FOREIGN PATENT DOCUMENTS

| | | |
|---|---|---|
| CN | 1410407 A | 4/2003 |
| CN | 1560012 A | 1/2005 |
| CN | 1597654 A | 3/2005 |
| CN | 103980248 A | 8/2014 |
| CN | 103980265 A | 8/2014 |
| EP | 0216279 | 9/1968 |
| JP | 2926768 B2 | 7/1999 |
| WO | 01/58845 A1 | 8/2001 |
| WO | 2013/036911 A1 | 3/2013 |
| WO | 2014/008257 A2 | 1/2014 |
| WO | 2014/158838 A1 | 10/2014 |

OTHER PUBLICATIONS

Minisci, Francesco et al., Highly Selective and Efficient Conversion of Alkyl Aryl and Alkyl Cyclopropyl Ketones to Aromatic and Cyclopropane Carboxylic Acids by Aerobic Catalytic Oxidation: A Free-radical Redox Chain Mechanism, Synlett 2002, No. 4, pp. 610-612.

Nakamura, Ryota et al., Selective Oxidation of Acetophenones Bearing Various Functional Groups to Benzoic Acid Derivatives with Molecular Oxygen, Adv. Synth. Catal. 2009, 351, pp. 1677-1684.

Partenheimer, Walt, The Complex Synergy of Water in Metal/Bromide Autoxidations. Part II. Effect of Water and Catalyst on the Aerobic Oxidation of Benzaldehydes and the Effect of Water on the Elementary Catalytic Pathways, Adv. Synth. Catal. 2005, 347, pp. 580-590.

(Continued)

*Primary Examiner* — Golam M Shameem
(74) *Attorney, Agent, or Firm* — Stinson LLP; Lawrence M. Lavin, Jr.

(57) ABSTRACT

Provided herein are processes for the preparation of heteroaryl carboxylic acids.

19 Claims, No Drawings

(56) References Cited

OTHER PUBLICATIONS

Partenheimer, Walt, The Aerobic Oxidative Cleavage of Lignin to Produce Hydroxy-aromatic Benzaldehydes and Carboxylic Acids via Metal/Bromide Catalysts in Acetic Acid/Water Mixtures, Adv. Synth. Catal. 2009, 351, pp. 456-466.

International Search Report and Written Opinion dated Aug. 25, 2017 relating to PCT Application No. PCT/US17/23322, 11 pages.

Dhar, P., et al., "Synthesis, Antimicrobial Evaluation, and Structure-Activity Relationship of α-Pinene Derivatives," 2014, J Agric Food Chem, 62:3548-3552, 5 pages.

Graf, R., "Umsetzungen Mit Olefinen und Aldehyden; Uber B-Lactame," 1963, Liebigs Ann Chem Bd, 661:111-161, 47 pages.

Gronowitz, S., et al., "Some Substitution Reactions of 2-(2'-Thienyl)pyrimidine and 2-(3'-Thienyl)pyrimidine," 1977, Acta Chemica Scandinavica, B, 31:771-780, 10 pages.

Jones, L.W., et al., "Rearrangements of Some New Hydroxamic Acids Related to Heterocyclic Acids and to Diphenyl- and Triphenyl-Acetic Acids." 1921, JACS, 43/11:2422-2448, 27 pages.

Maksay, G., et al., "Synthesis of Heteroaromatic Tropeines and Heterogeneous Binding to Glycine Receptors," 2009, Bioorg Med Chem, 17/19:6872-6878, Abstract Only, 1 page.

Vebrel, J., et al., "Synthese de methoxycarbonylindenes, dihydro-1,2 napthalenese et benzocycloheptene. Obtention des indanone-1, des tetralones-1 et de la benzosuberone correspondantes," 1982, Bulletin de la Societe Chimique de France, 34:II-116-II-124, 9 pages.

Vorbruggen, H., et al., "The Introduction of Nitrile-Groups into Heterocycles and Conversion of Carboxylic Groups into their Corresponding Nitriles with Chlorosulfonylisocyanate and Triethylamine," 1994, Tetrahedron, 50/22:6549-6558, 10 pages.

Xie, Shui-long et al., Study on Preparation of Benzoic Acid by Catalytic Oxidation of Benzaldehyde, Biomass Chemical Engineering, vol. 43, No. 2, Mar. 2009, pp. 23-26 (English abstract only).

Sathyanarayana, P., et al., "Copper Catalyzed Oxygen Assisted C(CNOH)-C(alkyl) Bond Cleavage: A Facile Conversion of aryl/aralkyl/vinyl Ketones to Aromatic Acids," 2015, Org Biomol Chem, 13:9681-9685, 5 pages.

* cited by examiner

PROCESSES FOR THE PREPARATION OF HETEROARYL CARBOXYLIC ACIDS

REFERENCE TO RELATED APPLICATIONS

This application is a 371 National Stage Application of International PCT Application No. PCT/US2017/023322, filed Mar. 21, 2017, which claims the benefit of U.S. Provisional Application No. 62/312,907, filed Mar. 24, 2016, and U.S. Provisional Application No. 62/423,357, filed Nov. 17, 2016, the contents of which are incorporated herein by reference.

FIELD

Provided herein are processes for the preparation of heteroaryl carboxylic acids that are useful, for example, in the preparation of heteroaryl acyl chlorides, such as 2-thiophenecarbonyl chloride.

BACKGROUND

Heteroaryl carboxylic acids are useful as starting materials and reagents in the preparation of a wide variety of industrially useful compounds. For example, U.S. Pub. No. 2014/0039197 A1 reports that heteroaryl acyl chlorides prepared from heteroaryl carboxylic acids can be reacted with N-hydroxyamidines in the preparation of 3,5-disubstituted-1,2,4-oxadiazoles, which are useful for, in part, nematode control in agriculture. For example, heteroaryl carboxylic acids can be used to prepare 2-thiophenecarbonyl chloride, which is useful in the preparation of tioxazafen (3-phenyl-5-(2-thienyl)-1,2,4-oxadiazole) by reaction with benzamide oxime. While methods for preparing heteroaryl carboxylic acids are known in the art, alternative routes that may result in a more efficient synthesis are highly desirable.

Citation of any reference herein is not to be construed as an admission that such reference is prior art to the present application.

SUMMARY

Provided herein are processes for the preparation of heteroaryl carboxylic acids of Formula II

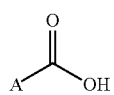

Formula II wherein A is an optionally independently substituted heteroaryl. The heteroaryl can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

For example, in one embodiment, the process comprises contacting a compound of Formula Ia

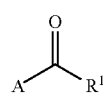

Formula Ia with oxygen in the presence of a catalyst component in an oxidation reaction zone comprising a liquid medium, wherein $R^1$ is $C_1$-$C_6$ alkyl; A is a heteroaryl which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; and wherein the catalyst component comprises a first transition metal ion selected from the group consisting of cobalt, copper, manganese, iron, zinc, zirconium, nickel, palladium, cadmium, and mixtures thereof.

In another embodiment, the process comprises contacting a compound of Formula Ia-i

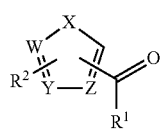

Formula Ia-i with oxygen in the presence of a catalyst component in an oxidation reaction zone comprising a liquid medium, wherein X is S, O, NC(O)O$R^b$, or NC(O)$R^b$; $R^b$ is $C_1$-$C_6$ alkyl or aryl; W, Y, and Z are each independently selected from the group consisting of N, C, and C(H); $R^1$ is $C_1$-$C_6$ alkyl; and $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$, $R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to W and Y or Y and Z; and wherein the catalyst component comprises a first transition metal ion selected from the group consisting of cobalt, copper, manganese, iron, zinc, zirconium, nickel, palladium, cadmium, and mixtures thereof.

In another embodiment, the process comprises contacting an acetylthiophene compound of Formula Ia-ii

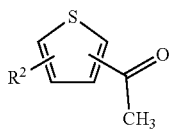

Formula Ia-ii with oxygen in the presence of a catalyst component in an oxidation reaction zone comprising a liquid medium, wherein $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$, wherein $R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to the two adjacent carbons of the thiophene ring; and wherein the catalyst component comprises a first transition metal ion from the group consisting of cobalt, copper, manganese, iron, zinc, zirconium, nickel, palladium, cadmium, and mixtures thereof.

In another embodiment, the process comprises reacting a heteroaromatic compound of Formula A-H with acetic anhydride in the presence of a cation ion exchange resin in an acylating reaction zone to produce a product mixture comprising a compound of Formula Ia-a;

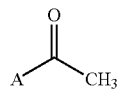

Formula Ia-a and contacting the compound of Formula Ia-a with oxygen in the presence of a catalyst component in the oxidation reaction zone comprising a liquid medium comprising acetic acid and acetic anhydride, wherein A is a heteroaryl which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; and wherein the cation exchange resin is a sulfonic acid-type cation exchange resin; and the catalyst component comprises a first transition metal ion selected from the group consisting of cobalt, copper, manganese, iron, zinc, zirconium, nickel, palladium, cadmium, and mixtures thereof.

In another embodiment, the process comprises contacting a compound of Formula Ib-i

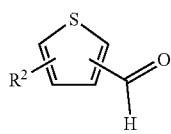

Formula Ib-i with oxygen in the presence of a catalyst component in an oxidation reaction zone comprising a liquid medium, wherein $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to the two adjacent carbons of the thiophene ring; and wherein the catalyst component comprises a first transition metal ion from the group consisting of cobalt, copper, manganese, iron, zinc, zirconium, nickel, palladium, cadmium, and mixtures thereof.

In a further embodiment, the process is directed to a preparation of a heteroaryl acyl chloride of Formula III,

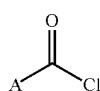

Formula III and comprises chlorinating the heteroaryl carboxylic acid of Formula II, prepared by the processes described herein, by reacting a chlorinating agent with the heteroaryl carboxylic acid dissolved in a chlorination medium comprising an organic solvent; wherein A is a heteroaryl which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In a further embodiment, the process is directed to the preparation of a 3,5 disubstituted 1,2,4-oxadiazole of Formula IV or a salt thereof,

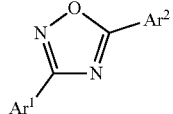

Formula IV and comprises reacting an N-hydroxyamidine of Formula V, or a tautomeric form thereof,

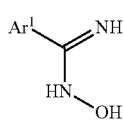

Formula V with 2-thiophenecarbonyl chloride prepared by the processes described herein; wherein $Ar^1$ is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl.

In a further embodiment, the process is directed to the preparation of a 3,5-disubstituted 1,2,4-oxadiazole of Formula IV or a salt thereof,

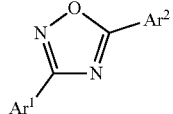

Formula IV and comprises reacting thiophene with acetic anhydride in an acylation reaction medium comprising a mineral acid or a cation exchange resin, thereby producing 2-acetylthiophene; contacting 2-acetylthiophene with a oxygen in an oxidation reaction zone comprising a liquid medium, thereby producing 2-thiophenecarboxylic acid; reacting 2-thiophenecarboxylic acid dissolved in a chlorination medium comprising an organic solvent with thionyl chloride, thereby producing 2-thiophenecarbonyl chloride; and reacting 2-thiophenecarbonyl chloride with an N-hydroxyamidine of Formula V, or a tautomeric form thereof,

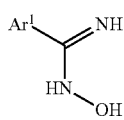

Formula V thereby producing a 3,5-disubstituted 1,2,4-oxadiazole or a salt thereof; wherein $Ar^1$ is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl.

In a further embodiment, the process is directed to the preparation of a 3,5-disubstituted 1,2,4-oxadiazole of Formula IV or a salt thereof,

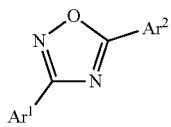

Formula IV and comprises reacting thiophene with dimethylformamide in the presence of phosgene or phosphoryl chloride in a reaction medium comprising an organic solvent, thereby producing 2-thiophenecarboxaldehyde; contacting 2-thiophenecarboxyaldehyde with oxygen in an oxidation reaction zone comprising a liquid medium, thereby producing 2-thiophenecarboxylic acid; reacting 2-thiophenecarboxylic acid dissolved in a chlorination medium comprising an organic solvent with thionyl chloride, thereby producing 2-thiophenecarbonyl chloride; and reacting 2-thiophenecarbonyl chloride with an N-hydroxyamidine of Formula V, or a tautomeric form thereof,

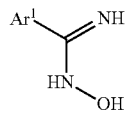

Formula V thereby producing a 3,5-disubstituted 1,2,4-oxadiazole or a salt thereof wherein $Ar^1$ is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl.

DETAILED DESCRIPTION

Unless defined otherwise, technical and scientific terms as used herein have the same meaning as commonly understood by one of ordinary skill in the art.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons, which can be optionally independently substituted. Non-limiting examples of $C_1$-$C_{10}$ alkyl groups include methyl, ethyl, propyl, isopropyl, butyl, sec-butyl, tert-butyl, 3-pentyl, hexyl and octyl groups, each of which can be optionally independently substituted.

The term "haloalkyl" as employed herein, by itself or as part of another group, refers to an alkyl group, as defined herein, substituted with at least one halogen. Non-limiting examples of haloalkyl groups include trifluromethyl and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy.

The term "haloalkoxy" as employed herein, by itself or as part of another group, refers to an alkoxy group as defined herein, wherein the alkyl moiety of the alkoxy group is further substituted with at least one halogen. Non-limiting example of haloalkoxy groups include trifluoromethoxy, and 2,2-dichloroethoxy.

The term "alkylamino" as employed herein, by itself or as part of another group, refers to an alkyl group, as defined herein, appended to the parent molecular moiety through a nitrogen atom.

The term "aryl", used alone or as part of a larger moiety, refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, refer to groups having 5 to 10 ring atoms, for example 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Unless otherwise indicated, the aryl and heteroaryl groups described herein can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

Various embodiments of the processes disclosed herein enable greater ease of production, milder reaction conditions, reduced reaction time cycles, fewer reaction intermediates, and/or significantly reduced capital equipment requirements.

In various embodiments, the processes comprise an oxidation step in which the compound of

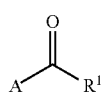

Formula I is oxidized to give the corresponding heteroaryl carboxylic acid of Formula II

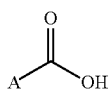

Formula II wherein A is a heteroaryl, which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino, and $R^1$ is selected from the group consisting of hydrogen and $C_1$-$C_6$ alkyl.

In various embodiments, the processes further comprise a step in which an optionally independently substituted heteroaryl is modified by the addition of a ketone or aldehyde group to give an intermediate compound of Formula I, wherein A is a heteroaryl, which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino, and $R^1$ is selected from the group consisting of hydrogen and $C_1$-$C_6$ alkyl. When $R^1$ is a $C_1$-$C_6$ alkyl, this step may be referred to herein as an acylation step. When $R^1$ is hydrogen, this step may be referred to herein as a formylation step.

In another embodiment, the process further comprises (a) an acylation step in which a heteroaromatic compound of the Formula A-H is acetylated with acetic anhydride to produce a product mixture comprising a compound of Formula Ia-a, acetic acid, and acetic anhydride;

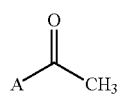

Formula Ia-a (b) a liquid medium modifying step in which the product mixture is modified with acetic acid to form an oxidation liquid medium; and (c) an oxidation step in which the compound of Formula Ia-a is oxidized to form the corresponding carboxylic acid of Formula II; wherein A is an optionally independently substituted heteroaryl. The heteroaryl can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In various embodiments, the processes further comprise a chlorination step in which the heteroaryl carboxylic acid of Formula II is converted to the heteroaryl acyl chloride of Formula III

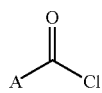

Formula III wherein A is a heteroaryl, which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^1$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

For example, one aspect of the present disclosure is directed to improved processes for the preparation of 2-thiophenecarbonyl chloride.

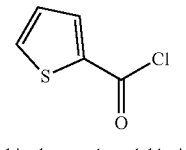

2-thiophenecarbonylchloride
(TCC)

Oxidation of the Heteroaryl Ketone to the Carboxylic Acid

In various embodiments, the processes disclosed herein comprise an oxidation step wherein a heteroaryl having a ketone substituent is oxidized to form the corresponding carboxylic acid. In some embodiments, the process comprises contacting a compound of Formula Ia

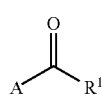

Formula Ia with oxygen in the presence of a catalyst component in a reaction zone (sometimes referred to herein as an oxidation reaction zone) comprising a liquid medium, thereby forming a compound of Formula II; wherein $R^1$ is a $C_1$-$C_6$ alkyl, and A is an optionally independently substituted heteroaryl. The heteroaryl can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, or —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, and $C_1$-$C_4$ alkylamino. For example, in one embodiment, 2-acetylthiophene is contacted with oxygen in a reaction zone comprising a liquid medium to produce 2-thiophenecarboxylic acid.

In some embodiments, the process includes oxidizing a compound of Formula Ia-i

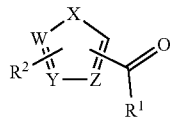

Formula Ia-i wherein X is S, O, NC(O)OR$^b$, or NC(O)R$^b$, R$^b$ is $C_1$-$C_6$ alkyl or aryl; W, Y, and Z are each independently selected from the group consisting of N, C, and C(H); R$^1$ is $C_1$-$C_6$ alkyl; R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or R$^2$ is aryl, fused to W and Y or Y and Z.

In some embodiments, for example, the compound of Formula Ia-i is a substituted thienyl, furanyl, or pyrrolyl ketone wherein X is S, O, NC(O)OR$^b$, or NC(O)R$^b$, R$^b$ is $C_1$-$C_6$ alkyl or aryl; W, Y, and Z are independently selected from the group consisting of C and C(H); R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In some embodiments, for example, the compound of Formula Ia-i is a substituted isothiazolyl, isoxazolyl, or pyrazolyl ketone wherein X is S, O, NC(O)OR$^b$, or NC(O)R$^b$, R$^b$ is $C_1$-$C_6$ alkyl or aryl; W is N, and Y and Z are independently selected from the group consisting of C and C(H); R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In some embodiments, for example, the compound of Formula Ia-i is a substituted thiazolyl, oxazolyl, or imidazolyl ketone wherein X is S, O, NC(O)OR$^b$, or NC(O)R$^b$, R$^b$ is $C_1$-$C_6$ alkyl or aryl; Y is N, and W and Z are independently selected from the group consisting of C and C(H); R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In some embodiments, for example, the compound of Formula Ia-i is a substituted 1,3,4-thiadiazolyl, 1,3,4-oxadiazolyl, or 1,2,4-triazolyl ketone wherein X is S, O, NC(O)OR$^b$, or NC(O)R$^b$, R$^b$ is $C_1$-$C_6$ alkyl or aryl; W is C, and Y and Z are each N; R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In some embodiments, for example, the compound of Formula Ia-i is a substituted 1,2,3-thiadiazolyl, 1,2,3-oxadiazolyl, or 1,2,3-triazolyl ketone wherein X is S, O, NC(O)OR$^b$, or NC(O)R$^b$, R$^b$ is $C_1$-$C_6$ alkyl or aryl; W and Y are each N, and Z is C; R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In other embodiments, the compound of Formula Ia-i is an aryl-fused 5-membered heteroaryl ketone, for example, a benzo-fused 5-membered heteroaryl ketone wherein X is S, O, NC(O)OR$^b$, or NC(O)R$^b$, R$^b$ is $C_1$-$C_6$ alkyl or aryl; W, Y, and Z are independently selected from the group consisting of N, C, and C(H); R$^1$ is $C_1$-$C_6$ alkyl; and R$^2$ is substituted phenyl, fused to W and Y or Y and Z. In some embodiments, for example, the benzo-fused 5-membered heteroaryl can be substituted benzo[b]thiophenyl or benzofuranyl when X is S or O; W, Y are each C, and Z is C or C(H); and R$^2$ is substituted phenyl, fused to W and Y. In some other embodiments, for example, the benzo-fused 5-membered heteroaryl can be substituted benzo[c]thiophenyl or isobenzofuranyl when X is S or O; W is C or C(H) and Y, Z are each C; and R$^2$ is substituted phenyl, fused to Y and Z.

In some embodiments, the compound of Formula Ia-i is a substituted thienyl or furanyl ketone wherein X is S or O; W, Y, and Z are independently selected from the group consisting of C and C(H); R$^1$ is $C_1$-$C_6$ alkyl; and R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, wherein R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino. In some embodiments, the compound of Formula Ia-i is a substituted thienyl ketone wherein X is S, and R$^1$ is $C_1$-$C_6$ alkyl. For example, in some embodiments, the compound of Formula Ia-i is an unsubstituted 2-thienyl ketone, wherein R$^1$ is $C_1$-$C_6$ alkyl.

In some embodiments, the compound is an acetylthiophene compound of Formula Ia-ii,

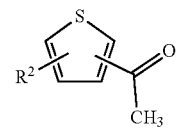

Formula Ia-ii wherein R$^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)R$^{21}$, R$^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or R$^2$ is aryl, fused to the two adjacent carbons of the thiophene ring.

For example, in some embodiments the compound of Formula Ia-ii is 2-acetylthiophene. In other embodiments, the compound of Formula Ia-ii is 3-acetylthiophene.

The compound of Formula Ia can be prepared by means known to those skilled in the art. In various embodiments, the processes comprise a first step in which an optionally independently substituted heteroaryl is modified by the addition of a ketone group to give an intermediate compound of Formula Ia. For example, 2-acetylthiophene can be prepared by reacting thiophene with acetic anhydride in an acylation reaction medium (e.g., a liquid medium). In some embodiments, the acylation reaction medium comprises a mineral acid. Non-limiting examples of suitable mineral acids include nitric acid, sulfuric acid, boric acid, perchloric acid, phosphoric acids, and hydrohalic acids. In an example embodiment, the acylation reaction medium comprises a phosphoric acid. U.S. Pat. No. 7,659,411 describes a process for preparing a 2-acetylthiophene compound in the absence of solvent by reacting a thiophene compound with acetic anhydride in the presence of a solid acid catalyst. The solid acid catalyst can be selected from the group consisting of zeolites, activated clays, and cation exchange resins, and combinations thereof. In other embodiments, 2-acetylthiophene can be prepared by reacting thiophene with acetic anhydride in the presence of a cation exchange resin. Suitable cation exchange resins are not particularly limited, and include, for example, perfluorosulfonic acid polymers, sulfonic acid polymers, and mixtures thereof. The cation exchange resins can be easily removed by filtration from the reaction product mixture and can be recycled for use in the acylation of thiophene. In one embodiment, the cation exchange resin is DOWER DR-2030. In another embodiment, the cation exchange resin is AMBERLYST™-15.

Oxidation of the Heteroaryl Aldehyde to the Carboxylic Acid

In various embodiments, the processes disclosed herein comprise a step wherein a heteroaryl having an aldehyde substituent is oxidized to form the corresponding carboxylic acid. Specifically, in some embodiments, the process comprises contacting a compound of Formula Ib

Formula Ib with oxygen in the presence of a catalyst component in a reaction zone comprising a liquid medium, thereby forming a compound of Formula II; wherein A is an optionally independently substituted heteroaryl. The heteroaryl can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino. For example, in one embodiment, 2-thiophenecarboxaldehyde is contacted with oxygen in a reaction zone comprising a liquid medium to produce 2-thiophenecarboxylic acid.

In some embodiments, for example, the compound of Formula Ib is a thiophenecarboxaldehyde of Formula Ib-i

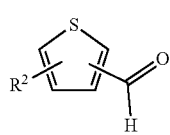

Formula Ib-i wherein: $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$, wherein $R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to the two adjacent carbons of the thiophene ring For example, in some embodiments the compound of Formula Ib-i is 2-thiophenecarboxaldehyde. In other embodiments, the compound of Formula Ib-i is 3-thiophenecarboxaldehyde.

The compound of Formula Ib can be prepared by means known to those skilled in the art. In various embodiments, the processes comprise a first step in which an optionally independently substituted heteroaryl is modified by the addition of an aldehyde group to give an intermediate compound of Formula Ib. For example, 2-thiophenecarboxaldehyde can be prepared by reacting thiophene with N,N-dimethylchloromethyliminium chloride in a formylation reaction medium. The N,N-dimethylchloromethyliminium chloride can also be generated in-situ by dimethylformamide in the presence of phosgene or phosphoryl chloride in the formylation reaction medium. In some embodiments, 2-thiophenecarboxaldehyde can be prepared by reacting thiophene with dimethylformamide in the presence of phosgene or phosphoryl chloride in a formylation reaction medium. In some embodiments, the formylation reaction medium comprises an organic solvent. Non-limiting examples of organic solvents in which the reaction can be carried out include aliphatic hydrocarbons such as hexane and heptane; organic chlorinated hydrocarbons such as methylene chloride, chloroform, 1,1-dichloroethane, and 1,2-dichloroethane; and other solvents such as acetonitrile and dialkylethers.

Organic Solvent

In some embodiments, the compound of Formula I (for example, the compound of Formula Ia or Ib) can be dissolved in a liquid medium comprising an organic solvent prior to the contacting step. In other embodiments, the compound of Formula I can be added into a liquid medium comprising an organic solvent during the contacting step. Generally, solvents used to form the liquid medium can be selected on the basis of one or more criteria to facilitate simplification and overall economics of the process. In general, the process steps described herein can be conducted utilizing batch, semi-batch, or continuous reactor designs.

For example, in some embodiments, the compound of Formula I is contacted with oxygen in a liquid medium comprising an alkanoic acid (e.g., a $C_2$-$C_6$ alkanoic acid). In some embodiments, the alkanoic acid comprises a $C_2$-$C_6$ linear or branched carboxylic acid. Non-limiting examples of suitable alkanoic acids include acetic acid, propionic acid, butanoic acid, pentanoic acid, and hexanoic acid. In some embodiments, the liquid medium comprises acetic acid.

Transition Metal Catalysts

In some embodiments, the compound of Formula I (for example, the compound of Formula Ia or Ib) is contacted with oxygen in the presence of a catalyst component comprising a first transition metal ion, which can be selected as described in further detail below. In some embodiments, the catalyst component further comprises a second transition metal ion.

A. Transition Metal Catalysts for Oxidation of Heteroaryl Ketones

The first transition metal ion may comprise metal ions selected from the group consisting of manganese, iron, copper, zinc, zirconium, nickel, palladium, cadmium and mixtures thereof. In some embodiments, the first transition metal ion is selected from the group consisting of manganese, iron, and copper. In some embodiments, the first transition metal ion comprises manganese ions.

When the catalyst component comprises a second transition metal ion, the second transition metal ion may comprise metal ions selected from the group consisting of cobalt, iron, copper, zinc, zirconium, nickel, palladium, cadmium and mixtures thereof. In some embodiments, the second transition metal ion is selected from the group consisting of cobalt, iron, and copper. In some embodiments, the second transition metal ion comprises cobalt ions.

When the catalyst component comprises a second transition metal ion, the first transition metal ion and the second transition metal ion are not the same. In some embodiments, the ratio of the first transition metal ion to the second transition metal ion in the reaction zone is no less than 0.1:1. For example, the ratio of the first transition metal ion to the second transition metal ion can be at least about 0.1:1, at least about 1:1, at least about 2:1, at least about 3:1, at least about 4:1, at least about 5:1, at least about 6:1, at least about 7:1, at least about 8:1, at least about 9:1, or at least about 10:1. In some embodiments, the ratio of the first transition metal ion to the second transition metal ion is from 0.1:1 to about 100:1, from 1:1 to about 100:1, from 1:1 to about 50:1, from 1:1 to about 40:1, from 1:1 to about 30:1, from 1:1 to about 20:1, or from 3:1 to about 15:1.

In some embodiments, the first transition metal ion is present in the liquid medium in an amount of from about 0.001 mol % to about 5 mol %, based on the compound of Formula Ia. For example, the first transition metal ion can be present in an amount 0.01 mol % to about 5 mol %, from about 0.1 mol % to about 5 mol %, from about 0.5 mol % to about 5 mol %, or from about 1 mol % to about 5 mol %.

In some embodiments, the second transition metal ion is present in the liquid medium in an amount of from about 0.001 mol % to about 5 mol %, based on the compound of Formula Ia. For example, the second transition metal ion can be present in an amount of from about 0.01 mol % to about 5 mol %, from about 0.1 mol % to about 5 mol %, from about 0.5 mol % to about 5 mol %, or from about 1 mol % to about 5 mol %, from about 0.1 mol % to about 1 mol %, or from about 0.1 mol % to about 0.5 mol %.

B. Transition Metal Catalysts for Oxidation of Heteroaryl Aldehydes

The first transition metal ion may comprise metal ions selected from the group consisting of cobalt, iron, copper, zinc, zirconium, nickel, palladium, cadmium and mixtures thereof. In some embodiments, the first transition metal ion is selected from the group consisting of cobalt, iron, and copper. In some embodiments, the first transition metal ion comprises cobalt ions.

When the catalyst component comprises a second transition metal ion, the second transition metal ion may comprise metal ions selected from the group consisting of manganese, iron, copper, zinc, zirconium, nickel, palladium, cadmium and mixtures thereof. In some instance, the second transition metal ion is selected from the group consisting of manganese, iron, and copper. In some embodiments, the second transition metal ion comprises manganese ions.

When the catalyst component comprises a second transition metal ion, the first transition metal ion and the second transition metal ion are not the same. In some embodiments, the ratio of the first transition metal ion to the second transition metal ion in the reaction zone is no less than 0.1:1. For example, the ratio of the first transition metal ion to the second transition metal ion can be at least about 0.1:1, at least about 1:1, at least about 2:1, at least about 3:1, at least about 4:1, at least about 5:1, at least about 6:1, at least about 7:1, at least about 8:1, at least about 9:1, or at least about 10:1. In some embodiments, the ratio of the first transition metal ion to the second transition metal ion is from 0.1:1 to about 100:1, from 1:1 to about 100:1, from 1:1 to about 50:1, from 1:1 to about 40:1, from 1:1 to about 30:1, from 1:1 to about 20:1, or from 3:1 to about 15:1.

In some embodiments, the first transition metal ion is present in the liquid medium in an amount of from about 0.001 mol % to about 5 mol %, based on the compound of Formula Ib. For example, the first transition metal ion can be present in an amount of 0.01 mol % to about 5 mol %, from about 0.1 mol % to about 5 mol %, from about 0.5 mol % to about 5 mol %, or from about 1 mol % to about 5 mol %.

In some embodiments, the second transition metal ion is present in the liquid medium in an amount of from about 0.001 mol % to about 5 mol %, based on the compound of Formula Ib. For example, the second transition metal ion can be present in an amount of from about 0.01 mol % to about 5 mol %, from about 0.1 mol % to about 1 mol %, or from about 0.1 mol % to about 0.5 mol %.

C. Introduction of Transition Metal Catalysts to the Oxidation Reaction Zone

The first and/or second transition metal ions can be introduced to the liquid medium as a salt in the form of anhydrous or hydrate thereof. For example, the first and/or second transition metal ion can be introduced to the liquid medium in the salt form of a halide, a $C_1$-$C_6$ alkanoate, a nitrate, a carbonate, or a combination thereof. In some embodiments, the first and/or second transition metal ion can be introduced to the liquid medium in the salt form of an alkanoate (e.g., as an acetate salt). For example, the catalyst component may comprise manganese acetate or cobalt acetate.

In some embodiments, the liquid medium comprises an alkanoic acid as the organic solvent, and the first and/or second transition metal ion is introduced to the liquid medium in the salt form of an alkanoate having the same anion as the alkanoic acid. For example, in some embodiments, the liquid medium comprises acetic acid and the first and second transition metal ions are added in the salt form of metal acetates. In some embodiments of the oxidation of heteroaryl ketones, the first transition metal salt is manganese acetate and the second transition metal salt is cobalt acetate. In other embodiments of the oxidation of heteroaryl aldehydes, the first transition metal salt is manganese acetate and the second transition metal salt is cobalt acetate.

The first and/or second transition metal ions can be introduced to the liquid medium prior to or during the contacting step.

D. Co-Catalyst

In some embodiments, the catalyst component comprises a first transition metal ion, and/or a second transition metal ion, and a co-catalyst. In one embodiment, the co-catalyst comprises zirconium. Without being bound to a particular theory, it is believed that adding zirconium to a transition metal catalyst system comprising cobalt as the first transition metal ion and/or second transition metal ion allows the cobalt concentration to be decreased while maintaining the same catalyst activity. At various cobalt concentrations, zirconium increases the catalyst concentration as the Zr/Co ratio increases, with a more pronounced effect at lower Zr/Co ratios.

Maintaining Oxygen Pressure

In some embodiments, the compound of Formula I (for example, the compound of Formula Ia or Ib) is contacted with oxygen in a reaction zone wherein the partial pressure of oxygen is at least about 1 atm. For example, the partial pressure of oxygen in the reaction zone can be at least about 2 atm, at least about 3 atm, at least about 4 atm, at least about 5 atm, at least about 6 atm, at least about 7 atm, at least about 8 atm, at least about 9 atm, or at least about 10 atm. In some embodiments, the partial pressure of oxygen in the reaction zone can be from about 1 atm to about 50 atm, from about 1 atm to about 40 atm, from about 1 atm to about 30 atm, from about 1 atm to about 20 atm, or from about 1 atm to about 10 atm.

In some embodiments, the process further comprises a means for purging the head space above the liquid medium within the reactor defining the reaction zone and introducing a source of oxygen-rich gas during the course of the reaction. Without being bound to a particular theory, it is believed that if carbon dioxide and other byproduct gases, generated during the oxidation reaction, are allowed to accumulate in the reaction zone, they can prevent oxygen molecules from efficiently reaching the reaction sites, significantly slowing the rate of reaction, and possible deactivating the metal catalyst. Additionally, it has been observed that the decrease in reaction rate due to byproduct gas accumulation becomes more severe as the process increases in scale.

Decrease in reaction rate can be addressed and a high rate of reaction consistently maintained by consistently maintaining an oxygen-rich atmosphere within the reaction zone. For example, the head space above the liquid medium within the reactor defining the reaction zone can be periodically purged and replaced with a fresh, oxygen-rich gas source. Alternatively, the head space above the liquid medium within the reactor defining the reaction zone can be continuously purged, and a source of oxygen-rich gas continuously introduced, to maintain a substantially constant pressure within the reaction zone.

In some embodiments, the source of oxygen-rich gas is substantially pure oxygen. In other embodiments, a gas source having a lower oxygen content (e.g., air) can be used, but a higher gas pressure in the reaction zone may be required to achieve the desire partial pressure of oxygen for the oxidation reaction. In addition, it may require frequent or continuous purging of the gas phase in the reaction zone to maintain an acceptably high reaction rate.

Process Temperature

The oxidation reaction can be carried out at a temperature of from about 70° C. to about 150° C. For example, the oxidation reaction can be carried out at a temperature from about 70° C. to about 150° C., from about 80° C. to about 140° C., from about 90° C. to about 130° C., from about 100° C. to about 120° C., or from about 110° C. to about 120° C.

Co-Reductants and Promotors

In some embodiments, the liquid medium further comprises a co-reductant. The co-reductant is used to denote a material which is capable of being oxidized along with the desired reactant. In some embodiments, if the concentration of the compound of Formula I (for example, the compound of Formula Ia or Ib) is sufficiently high in a solvent-diluted reaction, for example, at the beginning of the reaction, the compound acts as its own co-reductant. As the oxidation proceeds, however, and the concentration is reduced, it has been found necessary to add another material to the reaction mixture to maintain an efficient oxidation rate. Exemplar, useful co-reductants include for example lower alkyl aldehydes or dialkyl ketones. Non-limiting examples of suitable co-reductants include acetaldehyde, propionaldehyde, butyraldehyde, acetone, methyl ethyl ketone, diethyl ketone, and methyl isopropyl ketone.

For example, in some embodiments, the process comprises adding a co-reductant to the liquid medium during the contacting step. In some embodiments, the co-reductant can be added towards the end of oxidation reaction to assist with the conversion of the compound of Formula I to the corresponding carboxylic acid of Formula II. In general, the co-reductant is present in the liquid medium in an amount of 0.01 mol % to about 30 mol %, based on the compound of Formula I.

In some embodiments, the liquid medium further comprises a source of promoters to assist with the oxidation reaction. Promoters can be used to denote a salt which acts as a free radical transfer agent, for example, halide anions.

For example, in some embodiments the process comprises adding a hydrohalic acid to the liquid medium prior to or during the contacting step. Non-limiting examples of suitable hydrohalic acids include hydrofluoric acid, hydrochloric acid, hydrobromic acid, and hydroiodic acid. In some embodiments, the hydrohalic acid comprises hydrobromic acid. In other embodiments, the hydrohalic acid comprises hydrochloric acid.

In other embodiments, the process comprises adding a halide salt to the liquid medium prior to or during the contacting step. For example, the halide ions can be in the form of a calcium salt, a cesium salt, a lithium salt, a sodium salt, or a potassium salt. In some embodiments, the halide salt comprises bromide salts. Non-limiting examples of suitable bromide salts include calcium bromide, cesium bromide, lithium bromide, sodium bromide, and potassium bromide. In one embodiment, the halide salt comprises sodium bromide. In some embodiments, the halide salt comprises one or more chloride salts. Non-limiting examples of suitable chloride salts include calcium chloride, cesium chloride, lithium chloride, sodium chloride, and potassium chloride. In one embodiment, the halide salt comprises sodium chloride. In another embodiment, the halide salt comprises potassium chloride.

The halide ion can be present in the liquid medium in an amount of 0.01 mol % to about 10 mol %, based on the compound of Formula I. For some embodiments, for example, the halide ion is present in the liquid medium in an amount of from about 1 mol % to about 5 mol %, or from about 2 mol % to about 5 mol %.

In some embodiments, the liquid medium further comprises a zinc (II) salt. Without being bound by a particular theory, it is believed that the zinc salt may assist with the oxidation reaction. When hydrobromic acid or bromide salts are used as promotors, dibromide radicals (HBr2., Br2.−) are formed in the radical chain mechanism. Without being bound to a particular theory, it is believed that a zinc (II) salt, for example zinc acetate, can react with excess bromide ion to form ZnBr+. Therefore, the formation of excess bromide radical and its loss to the formation of undesired brominated by-products is minimized.

In some embodiments, the process comprises adding a zinc (II) salt to the liquid medium prior to or during the contacting step. For example, the zinc (II) salt can be in the salt form of a $C_2$-$C_6$ alkanoic acid. Non-limiting examples of suitable zinc alkanoic salts include zinc acetate, zinc propionate, zinc butanoate, zinc pentanoate, and zinc hexanoate. In some embodiments, the zinc (II) salt comprises zinc acetate. In one embodiment, 2-acetylthiophene or 2-thiophenecarboxylaldehyde can be oxidized in the liquid medium comprising acetic acid, bromide, and zinc acetate, wherein the formation of 5-bromothiophene-2-carboxylic acid is minimized.

The zinc (II) salt can be present in the liquid medium in an amount of 0.1 mol % to about 10 mol %, from about 1 mol % to about 5 mol %, or from about 2 mol % to about 5 mol %, based on the compound of Formula I.

In some embodiments, for example, the first transition metal ion and the second transition metal ion can be optionally generated from the transition metals in the oxidation liquid medium comprising a hydrohalic acid, as described in detail above.

In some embodiments, for example, the process comprises adding nitric acid to the liquid medium prior to or during the contacting step. For example, nitric acid can be present in the liquid medium in an amount of 0.01 mol % to about 10 mol %, based on the compound of Formula I.

In other embodiments, the process comprises adding a nitrate salt to the liquid medium prior to or during the contacting step. Without being bound to a particular theory, the use of a nitrate salt in the place of a halide (e.g., a hydrohalic acid or a halide salt) may eliminate the formation of undesired halogenated by-products. Non-limiting examples of suitable nitrate salts include calcium nitrate, cesium nitrate, lithium nitrate, sodium nitrate, and potassium nitrate. In one embodiment, the nitrate salt comprises sodium nitrate. The nitrate salt can be present in the liquid medium in an amount of 0.1 mol % to about 10 mol %, from about 1 mol % to about 5 mol %, or from about 2 mol % to about 5 mol %, based on the compound of Formula I.

Carboxylic Anhydride

In some embodiments, the liquid medium further comprises a carboxylic anhydride.

In some embodiments, the process comprises adding a carboxylic anhydride prior to or during the contacting step. The carboxylic anhydride can be a symmetrical carboxylic anhydride or an asymmetrical carboxylic anhydride. Non-limiting examples of suitable carboxylic anhydrides include acetic anhydride, acetic propionic anhydride, propionic anhydride, acetic butyric anhydride, and butyric anhydride. In some embodiments, the symmetrical carboxylic anhydride has the same alkyl group as the carboxylic acid in the liquid medium. In one embodiment, the symmetrical carboxylic anhydride is acetic anhydride when the liquid medium comprises acetic acid. In another embodiment, the symmetrical carboxylic anhydride is propionic anhydride when the liquid medium comprises propionic acid. In another embodiment, the liquid medium comprises acetic acid and acetic anhydride.

The carboxylic anhydride can be present in the liquid medium in an amount of from about 1 equivalent to about 2 equivalents, based on the compound of Formula Ia. For some embodiments, for example, the carboxylic anhydride is present in the liquid medium in an amount of from about 1.2 equivalents to about 1.6 equivalents.

In one embodiment, the liquid medium comprises acetic acid and acetic anhydride; and the compound of Formula Ia being oxidized is an acetylated heteroaryl compound (i.e., $R^1$ of Formula Ia is methyl). In another embodiment, the compound of Formula Ia being oxidized is Formula Ia-ii. In one embodiment, the compound of Formula Ia-ii being oxidized is 2-acetylthiophene. In another embodiment, the compound of Formula Ia-ii being oxidized is 3-acetylthiophene.

The acetic anhydride can be added to the liquid medium. Alternatively, the acetic anhydride can be introduced to the liquid medium from the prior step of the preparation of 2-acetylthiophene (e.g., the excess acetic anhydride at the end of reaction with thiophene).

At the end of oxidation reaction, any carboxylic anhydrides present in the liquid medium can be hydrolyzed by addition of water to the carboxylic acid corresponding to the anhydride. Alternatively, carboxylic anhydrides present in the liquid medium can also be hydrolyzed during the next step of isolation of the carboxylic acid of Formula II. A small amount of anhydrides (e.g., a symmetrical anhydride corresponding to the carboxylic acid of Formula II and/or a mixed anhydride corresponding to acetic acid and the carboxylic acid of Formula II) may form in the liquid medium that further comprises a carboxylic anhydride. However, these anhydride species can also be hydrolyzed to the carboxylic acid of formula II at the end of reaction by the addition of water, or during the next step of isolation of the carboxylic acid of Formula II.

Conversion of the Heteroaromatic to the Carboxylic Acid

In various embodiments, the processes disclosed herein comprise an acylation step wherein a heteroaromatic compound of Formula A-H is acetylated with acetic anhydride in the presence of a cation ion exchange resin in an acylation liquid zone to produce a product mixture comprising a compound of Formula Ia, wherein $R^1$ is methyl; a liquid medium modifying step wherein the product mixture is modified to form an oxidation liquid medium; and an oxidation step wherein the compound of Formula Ia-a is oxidized to form the corresponding carboxylic acid.

In some embodiments, the process comprises reacting a heteroaromatic compound of Formula A-H with acetic anhydride in the presence of a cation ion exchange resin in an acylating reaction zone to produce a product mixture comprising a compound of Formula Ia-a;

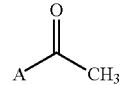

Formula Ia-a and contacting the compound of Formula Ia-a with oxygen in the presence of a catalyst component in an oxidation reaction zone comprising a liquid medium comprising acetic acid and acetic anhydride, thereby forming a compound of Formula II:

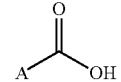

Formula II wherein A is an optionally independently substituted heteroaryl. The heteroaryl can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$; $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino.

In some embodiments, the process further comprises one or more of the following steps: (a) removing the cation exchange resin from the product mixture; (b) adding acetic acid to the product mixture, thereby forming the liquid medium; and (c) transferring the liquid medium to the oxidation reaction zone.

In some embodiments, the heteroaromatic compound of Formula A-H is a monocyclic 5-membered heteroaryl or an aryl-fused 5-membered heteroaryl compound, and the compound of Formula Ia-i-a:

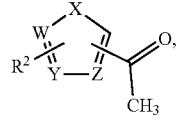

Formula Ia-i-a wherein each of X, W, Y, Z and $R^2$ may be selected as defined above with respect to Formula Ia-i.

In one embodiment, the heteroaromatic compound of Formula A-H is a substituted thiophene or furan, and the compound of Formula Ia-i-a is a substituted thienyl or furanyl methyl ketone wherein X is S or O; W, Y, and Z are independently selected from the group consisting of C and C(H); and $R^2$ may be selected as defined above with respect to Formula Ia-i. In one embodiment, the compound of Formula Ia-i-a is a substituted acetylthiophene of Formula Ia-ii:

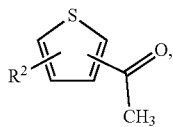

Formula Ia-ii wherein $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$, $R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to the two adjacent carbons of the thiophene ring.

In another embodiment, the process comprises reacting thiophene with acetic anhydride in the presence of a cation ion exchange resin to produce a product mixture comprising 2-acetylthiophene (i.e., Formula Ia-ii wherein $R^2$ is hydrogen); and contacting 2-acetylthiophene with oxygen in the presence of a catalyst component in an oxidation reaction zone comprising a liquid medium comprising acetic acid and acetic anhydride, thereby forming 2-thiophenecarboxylic acid.

Cation exchange resins useful in the processes described herein include, for example, styrene-divinylbenzene types of strong acid ion exchange resins such as DOWEX 50WX8, DOWEX 50WX4, DOWEX 50WX2, DOWEX M-31, DOWEX MONOSPHERE M-31, DOWEX DR-2030 and DOWEX MONOSPHERE DR-2030 catalysts commercially available from The Dow Chemical Company. In one embodiment, the cation exchange resin is DOWEX DR-2030.

Other examples of commercially available cation exchange resins useful in the processes described herein include DIAION SK104, DIAION SKIB. DIAION PK208, DIAION PK212 and DIAION PK216 manufactured by Mitsubishi Chemical Industries, Limited; AMBERLYST™-15, AMBERLYST™-35, AMBERLYST™-121, AMBERLYST™-232 and AMBERLYST™-131 manufactured by The Dow Chemical Company; T-38, T-66 and T-3825 manufactured by Thermax; LEWATIT K1131, LEWATIT K1221, LEWATIT K1261 and LEWATIT SC 104 manufactured by Lanxess; INDION 180 and INDION 225 manufactured by Ion Exchange India Limited; and PUROLITE CT-175 PUROLITE CT-222 and PUROLITE CT-122 manufactured by Purolite. In one embodiment, the cation exchange resin is AMBERLYST™-15.

The sulfonic acid-type cation exchange resin useful in the processes described herein can be, for example, a sulfonated styrene-divinyl benzene copolymer, a sulfonated crosslinked styrene polymer, a phenol formaldehyde-sulfonic acid resin, or a benzene formaldehyde-sulfonic acid resin.

The cation exchange resin can be used in gel, porous, or seeded forms. These resins can have narrow or broad particle size distributions. The cation exchange resin can also be sulfone cross-linked, shell functionalized and or contain greater than one sulfonic acid group per benzene ring. The process can be performed with one or more resin catalysts.

The cation exchange resins can be easily removed, for example by filtration, from the acetylation reaction product mixture and can be recycled for use in the next acylation reaction. In general, in order to reduce the loss of the reaction product, the removed cation exchange resins can be washed with acetic acid and the resulting wash eluent comprising acetic acid can be used in the modifying step to form a liquid medium comprising the compound of Formula Ia-a, acetic acid, and acetic anhydride.

In one embodiment, the acylation reaction can be carried out in neat acetic anhydride and acetic acid is subsequently formed as a part of the product mixture. In such embodiments, the acetic anhydride can be present in the acylation zone in an amount of from about 2 equivalents to about 5 equivalents, based on the heteroaromatic compound of Formula A-H. For one embodiment, for example, the carboxylic anhydride is present in the acylation zone in an amount of from about 2 equivalents to about 4 equivalents, or about 2 equivalents to about 3 equivalents.

The acylation reaction can be carried out at a temperature of from about 20° C. to about 100° C. For example, the acylation reaction can be carried out at a temperature from about 30° C. to about 80° C., from about 30° C. to about 70° C., from about 30° C. to about 60° C., from about 30° C. to about 50° C., from about 30° C. to about 40° C., from about 40° C. to about 70° C., from about 40° C. to about 60° C., or from about 40° C. to about 50° C.

In one embodiment, the acetic acid can be added to the product mixture in an amount of from about 1 equivalent to about 3 equivalents based on the heteroaromatic compound of Formula A-H; thereby forming the liquid medium comprising the compound of Formula Ia-a, acetic acid, and acetic anhydride. For some embodiments, for example, the amount of acetic acid added to the product mixture can be from about 1 equivalent to about 2 equivalents, or about 1 equivalent.

Transition metal catalysts can be selected as described in detail above. In one embodiment, the process described herein includes the oxidation reaction zone comprising a liquid medium comprising acetic acid and acetic anhydride that are modified and transferred from the acylation reaction zone after removing the cation exchange resins. In those embodiments, the first and second transition metal ions are added in the salt form of metal acetates. In one embodiment, the first transition metal salt is manganese acetate or a hydrate thereof; and the second transition metal salt is cobalt acetate or a hydrate thereof. Other parameters of the oxidation reaction, for example, maintaining oxygen pressure, process temperature, co-reductants and promotors, and effect of the carboxylic anhydride can be selected as described in detail above.

Isolation of the Carboxylic Acid

The compound of Formula II can be isolated from the reaction mixture by means known to those skilled in the art. For example, in some embodiments, the process steps to isolate the 2-thiophenecarboxylic acid (TCA) from the oxidation reaction may include these steps: filtration (e.g., filtering unwanted solids formed in the reaction), removal of organic solvent (e.g., acetic acid), extraction (e.g., partition of the crude product), and concentration to obtain the 2-thiophenecarboxylic acid.

Many common organic solvents are suitable for extraction of 2-thiophenecarboxylic acid after removal of acetic acid at the end of the oxidation reaction. As disclosed herein, in one embodiment, the organic solvent is selected so that the extraction of 2-thiophenecarboxylic acid and a chlorination step of converting 2-thiophenecarboxylic acid to 2-thiophenecarbonyl chloride (TCC) can be carried out in the same selected solvent. In some embodiments, the use of a single-solvent process for both extraction and the chlorination step provides a number of significant benefits, for example, less isolation, less solvent carry over, more efficient and convenient to operate. In one embodiment of the process described herein, a particular advantage is that it is not necessary to isolate the 2-thiophenecarboxylic acid for use in a subsequent step. In other embodiments, the solvent can be exchanged between the extraction and the chlorination steps, wherein suitable solvents are selected independently from each other.

In one embodiment, the organic solvent may form an azeotrope with water. The formation of an azeotrope facilitates removal, via e.g. evaporation or distillation, of the water in the 2-thiophenecarboxylic acid intermediate to substantially anhydrous conditions for effective use of the chlorinating reagent during subsequent conversion to the 2-thiophenecarbonyl chloride product.

Non-limiting examples of organic solvents suitable for use in extraction of 2-thiophenecarboxylic acid with the process described herein include $C_5$-$C_{10}$ alkane solvents, $C_1$-$C_{10}$ halogenated alkane solvents, $C_1$-$C_6$ alkylbenzenes, halogenated aromatic solvents, dialkyl ether solvents of the general formula R—O—R', wherein R and R' are each independently selected from $C_1$-$C_6$ alkyl, and ester solvents of the formula R—C(O)O—R' wherein R and R' are each independently selected from $C_1$-$C_6$ alkyl.

In some embodiments, the organic solvent comprises a $C_5$-$C_{10}$ alkane compound. The compound may comprise one or more $C_1$-$C_{10}$ linear, branched or cyclic alkyl groups. By way of non-limiting example, the organic solvent may comprise hexane, 2-methylhexane, or cyclohexane.

In some embodiments, the organic solvent comprises a $C_1$-$C_{10}$ halogenated alkane solvent. The compound may comprise one or more $C_1$-$C_{10}$ linear, branched or cyclic alkyl groups. In some embodiments, the compound may comprise one or more halogen substituents independently selected from F, Cl, and Br. For example, the compound may comprise from one to six halogen substituents. By way of non-limiting example, the organic solvent may comprise dichloromethane, dichloroethane, chloroform, or carbon tetrachloride.

In some embodiments, the organic solvent comprises a $C_1$-$C_6$ alkylbenzene compound. The compound may comprise one or more $C_1$-$C_6$ linear, branched or cyclic alkyl groups, each of which can be optionally independently substituted with one or more halogen substituents independently selected from F, Cl, and Br. For example, the compound may comprise from one to six halogen substituents. In some embodiments, the alkyl groups are saturated alkyl groups. By way of non-limiting example, the organic solvent may comprise toluene, o-xylene, p-xylene, m-xylene, xylenes, trimethylbenzene, or (trifluoromethyl)benzene.

In some embodiments, the organic solvent comprises a halogenated aromatic compound comprising one or more halogen substituents independently selected from F, Cl, and Br. For example, the compound may comprise from one to six halogen substituents. By way of non-limiting example, the organic solvent may comprise chlorobenzene, dichlorobenzene, chlorotoluene, or hexafluorobenzene.

In some embodiments, the organic solvent comprises a compound of the formula R—O—R' wherein R is selected from $C_4$-$C_6$ cycloalkyl and R' is methyl. For example, the organic solvent may comprise cyclopentyl methyl ether.

In other embodiments, the organic solvent comprises a compound of the formula R—O—R' wherein R and R' are each $C_3$-$C_6$ alkyl. For example, the organic solvent may comprise dibutyl ether.

In further embodiments, the organic solvent comprises an ester compound of the formula R—C(O)O—R' wherein R and R' are each independently selected from $C_1$-$C_6$ alkyl. For example, the organic solvent may comprise ethyl acetate, isopropyl acetate, butyl acetate, or isobutyl acetate.

The organic extract comprising 2-thiophenecarboxylic acid can be optionally washed with an additional aqueous hydrochloride solution.

Recovery of Transition Metal Catalysts

Recovery of the transition metal catalysts from the reaction product or waste stream would further enhance process economics. There are several methods reported for recovering the transition metal catalysts. For example, U.S. Pat. No. 4,910,175 describes a process for recovering cobalt and/or manganese catalysts via their oxalate salts. U.S. Pat. No. 6,255,510 describes a process for recovering the cobalt and/or manganese catalysts by treatment of acetic anhydride. Both of reported methods may be suitable for recovering the transition metal catalysts from the reaction product or waste stream for the processes descried herein.

Accordingly, in various embodiments, the process further comprises recovering the transition metal catalysts from the reaction product or the waste stream (e.g., aqueous solution used during the extraction).

Recycle of Organic Solvent

Recycle of the organic solvent (e.g., acetic acid) from the reaction mixture or waste stream would further enhance process economics. In one embodiment, the formic acid is removed in a $C_2$-$C_6$ alkanoic acid before recycling. In other embodiments, the removal of the formic acid in the liquid medium can be performed by addition of a carboxylic anhydride at the end of the oxidation reaction before removal of the alkanoic acid; when the alkanoic acid (e.g., acetic acid) is removed by distillation without treatment, the distillate can be treated with a carboxylic anhydride to remove formic acid before recycling. In one embodiment, the process further comprises treating the organic solvent (e.g., acetic acid) from the isolation step of the carboxylic acid with a carboxylic anhydride and recycling the treated organic solvent. In other embodiments, for example, the carboxylic anhydride is acetic anhydride and the organic solvent comprises acetic acid.

Conversion of the Carboxylic Acid to the Acyl Chloride

In various embodiments, the processes disclosed herein further comprise a chlorination step wherein the carboxylic acid compound of Formula II is chlorinated to form the corresponding acyl chloride of Formula III.

Non-limiting examples of chlorinating agents include thionyl chloride, oxalyl chloride, $POCl_3$, $PCl_5$, phosgene, and other known chlorinating agents. For example, in some embodiments, the chlorinating agent is thionyl chloride.

In some embodiments, the compound of Formula II is present in the form of a solution in an organic solvent. For example, in some embodiments, thionyl chloride is added to a chlorination reaction medium comprising the compound of Formula II dissolved in the organic solvent. In some embodiments, the reaction mixture is initially heterogeneous or multi-phasic, but becomes substantially homogeneous or monophasic after a sufficient portion of the chlorinating reagent has been added.

In some embodiments, the reaction is carried out in the presence of a catalyst that promotes the formation of the Formula III product. Non-limiting examples of catalysts include amides, imides, amines, quaternary ammonium salts and ureas. For example, in some embodiments, the chlorination reaction medium may comprise an N,N-disubstituted amide such as N,N-dimethyl formamide or N-methylpyrrolidone; a N-monosubstituted amide such as N-methyl formamide or N-methylacetamide; a tertiary amine such as pyridine or triethylamine; a secondary amine such as pyrrolidine or diethylamine; and/or a substituted urea such as tetramethyl urea. For example, in some embodiments, the chlorination reaction medium comprises a catalytic amount of N,N-dimethylformamide, wherein the molar percentage of N,N-dimethylformamide to the compound of Formula II is from about 1 mol % to about 5 mol %.

To maximize the conversion of the carboxylic acid compound of Formula II to the acyl chloride of Formula III, the reaction can be carried out with the chlorinating reagent present in molar excess relative to the compound of Formula II. In some embodiments, the molar ratio of chlorinating reagent to the compound of Formula II, in terms of the amount of each reactant added to the chlorination reaction medium, is less than about 2:1. For example, in some embodiments, the molar ratio of chlorinating reagent to the compound of Formula II, in terms of the amount of each reactant added to the chlorination reaction medium, is from about 1:1 to about 2:1, from about 1.5:1 to about 2:1, from about 1.1:1 to about 1.5:1, or from about 1.1:1 to about 1.25:1.

In some embodiments, the reaction of the compound of Formula II with the chlorinating agent is carried out at a temperature below the boiling point of the organic solvent present in the chlorination reaction medium. In some embodiments, the reaction of the compound of Formula II with the chlorinating reagent is carried out at a temperature of from about 50° C. to about 80° C., or from about 60° C. to about 70° C.

Production of 3,5-Disubstituted 1,2,4-Oxadiazoles

In various embodiments, the process may further comprise steps for producing a 3,5-disubstituted 1,2,4-oxadiazole or a salt thereof from Formula III. Methods for the preparation of 3,5-disubstituted-1,2,4-oxadiazoles that utilize acyl chlorides as a starting material are disclosed in U.S. Pub. No. 2014/0039197 A1, the entire contents of which are herein incorporated by reference.

Although the disclosure herein has been described with reference to particular aspects, it is to be understood that these aspects are merely illustrative of the principles and applications of the present disclosure. It is therefore to be understood that numerous modifications may be made to the illustrative aspects and that other arrangements may be devised without departing from the spirit and scope of the present disclosure as defined by the appended claims. Therefore, it is intended that the present disclosure not be limited to the particular aspects disclosed as the best mode contemplated for carrying out the present disclosure, but that the present disclosure will include all aspects falling within the scope and spirit of the appended claims.

The following examples are to be considered as merely illustrative, and are not intended to limit the scope of this disclosure.

EXAMPLES

Example 1

Analytical Methods

A. Reverse-Phase High-Performance Liquid Chromatography (RP-HPLC) Method

RP-HPLC analysis used to monitor reactions was conducted on an AGILENT 1260 INFINITY Analytical-Scale LC/MS Purification System equipped with a diode array UV detector and monitored at 230 nm and 280 nm.

B. Nuclear Magnetic Resonance Method

Nuclear magnetic resonance analysis was run on a BRUKER 600 MHz instrument. Deuterated solvents from Cambridge Isotope Laboratories, Ltd., including methanol-$d_4$, chloroform-d, and dimethylsulfoxide-$d_6$, were used as required.

C. Gas Chromatography Flame Ionization Detection (GC-FID) Method

Gas Chromatography Flame Ionization Detection (GC-FID) analysis was used to determine the purity and impurity profiles of 2-thiophenecarboxylic acid and thiophene-2-carbonyl chloride. Thiophene-2-carbonyl chloride samples were diluted in hexane and analyzed on an AGILENT 7890B GC-FID system with AGILENT 7693 autosampler.

Example 2

Preparation of 2-Thiophenecarboxylic Acid from 2-Acetylthiophene via Oxidation

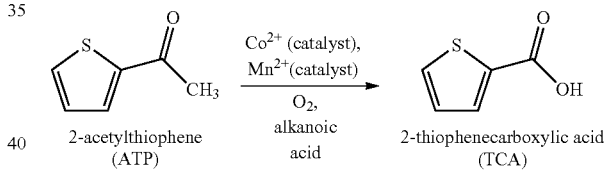

The following are general procedures for the preparation of 2-thiophenecarboxylic acid from 2-acetylthiophene by oxidation. The transition metal ion catalysts (e.g., a salt form, an amount, and a ratio of $Co^{2+}$ and $Mn^{2+}$), the organic solvent of the reaction (e.g., a $C_2$-$C_6$ alkanoic acid), the oxygen pressure, and the reaction temperature can vary during the process of the preparation. The following Experiments 2.1, 2.2, 2.3, and 2.4 are representative procedures with several variable parameters.

Experiment 2.1: Oxidation Using Catalysts of $Co(NO_3)_2$ and $Mn(NO_3)_2$ in Propionic Acid Under Oxygen 2-Acetylthiophene (5.0 g, 39.6 mmol) was dissolved in propionic acid (40 mL). The transition metal ion catalysts, $Co(NO_3)_2 \cdot 6H_2O$ (346 mg, 1.2 mmol) and $Mn(NO_3)_2 \cdot 4H_2O$ (300 mg, 1.2 mmol), were added to the solution of 2-acetylthiophene. The resulting mixture was purged with oxygen and heated to 125° C. under oxygen at 1 atm. After heating at 125° C. for 4 hours, the RP-HPLC indicated the formation of 2-thiophenecarboxylic acid along with the remaining of 2-acetylthiophene. Additional metal ion catalysts of $Co(NO_3)_2 \cdot 6H_2O$ (230 mg, 0.79 mmol) and $Mn(NO_3)_2 \cdot 4H_2O$ (200 mg, 0.79 mmol) were added to the reaction mixture, and the resulting mixture was heated at 125° C. overnight. The RP-HPLC indicated the disappearance of 2-acetylthiophene with a clean formation of the desired product of 2-thiophenecarboxylic acid. After cooling to room temperature, the reaction mixture was filtered to remove the formed solids. The solvent was removed by evaporation, and the resulting solids were partitioned between water and ethyl acetate. The organic layer was dried over anhydrous magnesium sulfate and concentrated to provide the title compound as a solid. The GC-FID analysis showed that the obtained material contained 2-thiophenecarboxylic acid (98.7 area %) and 2-acetylthiophene (1.3 area %).

Experiment 2.2: Oxidation Using Catalysts of $Co(OAc)_2$ and $Mn(OAc)_2$ in Acetic Acid Under Oxygen 2-Acetylthiophene (5.0 g, 39.6 mmol) was dissolved in acetic acid (40 mL) in a pressure tube. The transition metal ion catalysts, $Co(OAc)_2.4H_2O$ (300 mg, 1.2 mmol) and $Mn(OAc)_2.4H_2O$ (294 mg, 1.2 mmol), were added to the solution of 2-acetylthiophene. The pressure tube containing the reaction mixture was evacuated under a vacuum, and then filled with oxygen and the oxygen pressure was maintained at 75 psi (i.e., 5.1 atm). The resulting mixture in the pressure tube was heated to 118° C. under oxygen at 75 psi. After heating at 118° C. for 3 hours, the oxygen uptake was observed to cease. The RP-HPLC indicated the reaction mixture had a composition of 2-thiophenecarboxylic acid (83 area %) and the remaining 2-acetylthiophene (approximately 6 area %). The isolation of the 2-thiophenecarboxylic acid was followed by the steps of cooling to room temperature, filtration of formed solids, removal of acetic acid, partition with water and ethyl acetate, and concentration.

Experiment 2.3: Oxidation Using Catalysts of $Co(OAc)_2$ and $Mn(OAc)_2$ in Acetic Acid Under Oxygen (with Continuous Purging)

A pressure reactor was equipped with a feed inlet, an oxygen inlet, an oxygen sparger, a thermocouple, a mechanical stirrer, a condenser, and a manifold containing a pressure gauge, pressure relief valve, and rupture disc. A solution of 2-acetylthiophene (30.0 g, 237.4 mmol), dissolved in acetic acid (240 mL), was placed in the pressure reactor. The transition metal ion catalysts, $Co(OAc)_2.4H_2O$ (1.78 g, 7.1 mmol) and $Mn(OAc)_2.4H_2O$ (1.75 g, 7.1 mmol), were added to the solution of 2-acetylthiophene. The pressure reactor containing the reaction mixture was evacuated under a vacuum, and then filled with oxygen and the oxygen pressure was maintained at 32 psi (i.e., 2.2 atm). The resulting mixture in the pressure reactor was heated to from 115° C. to 125° C. under oxygen at 32 psi. The oxygen uptake was observed to start at approximately 100° C. During the reaction, the reaction mixture in the pressure reactor was purged and refilled with fresh oxygen continuously. After rapid uptake of oxygen, the reaction mixture started self-heating and cooling may be necessary to maintain the desired reaction temperature. After heating at 115-125° C. for 4 hours, the oxygen uptake was observed to cease. After cooling to room temperature, the reaction mixture was filtered to remove the formed solids. The solvent was removed by evaporation, and the resulting solids were partitioned between water and diethyl ether. The organic layer was treated with active carbon, filtered, and then dried over anhydrous magnesium sulfate. After concentration, the title compound was obtained as a solid. The GC-FID analysis showed that the obtained material contained 2-thiophenecarboxylic acid (93 area %) and 2-acetylthiophene (3 area %).

Experiment 2.4: Oxidation Using Catalysts of $Co(OAc)_2$ and $Mn(OAc)_2$ in Acetic Acid Under Oxygen (with Continuous Purging) with/without an Initiation of the Reaction A pressure reactor was equipped with a feed inlet, an oxygen inlet, an oxygen sparger, a thermocouple, a mechanical stirrer, a condenser, and a manifold containing a pressure gauge, pressure relief valve, and rupture disc. A solution of 2-acetylthiophene (2.0 g, 15.8 mmol), dissolved in acetic acid (190 mL), was placed in the pressure reactor. The transition metal ion catalysts, $Co(OAc)_2.4H_2O$ (1.78 g, 7.1 mmol) and $Mn(OAc)_2.4H_2O$ (1.75 g, 7.1 mmol), were added to the solution of 2-acetylthiophene. The residues of the catalysts were rinsed with acetic acid (30 mL) and added to the reaction mixture. The feed inlet was connected with an additional funnel charged with the remaining 2-acetylthiophene (28.0 g, 221.9 mmol) in acetic acid (50 mL). The pressure reactor containing the reaction mixture was evacuated under a vacuum, and then filled with oxygen and the oxygen pressure was maintained at 32 psi (i.e., 2.2 atm). After the reaction was initiated, the ketone in the additional funnel was added into the reaction mixture containing catalysts at a temperature of 75-100° C. over a period of 30-45 minutes; during which, the oxygen pressure was maintained at a range of 30-35 psig. In general, the reaction was sufficiently exothermic during the 2-acetylthiophene addition to maintain the reaction temperature between 100° C. and 120° C., even when the heating source was removed. The reaction was completed in an hour after heating at 120° C. The reaction mixture in the pressure reactor was purged and refilled with fresh oxygen continuously during the reaction.

The initiation of the reaction, described above, is optional for a large scale process. Alternatively, the transition metal ion catalysts, and acetic acid can be mixed altogether in the pressure reactor and placed under oxygen without 2-acetylthiophene. After heating, 2-acetylthiophene can be added via the additional funnel to the initial mixture at a desired temperature and under the desired oxygen pressure.

After cooling to room temperature, the reaction mixture was filtered to remove the formed solids. The solvent was removed by evaporation, and the resulting solids were subjected to extraction for isolation of the desired product of 2-thiophenecarboxylic acid.

Example 3

Efficiency of Oxidation from 2-Acetylthiophene to 2-Thiophenecarboxylic Acid

Experiment 3.1

Experiment 2.2 of Example 2 was repeated on the same scale of 2-acetylthiophene (5 g), except that the oxygen pressure was at 60 psi (i.e., 4.1 atm).

Experiment 3.2

Experiment 2.2 of Example 2 was repeated on a scale of 2-acetylthiophene (10 g), and the oxygen pressure was at 60 psi (i.e., 4.1 atm).

Experiment 3.3

Experiment 2.2 of Example 2 was repeated on a scale of 2-acetylthiophene (10 g), and the oxygen pressure was at 70 psi (i.e., 4.8 atm).

Experiment 3.4

Experiment 2.3 of Example 2 was presented on the scale of 2-acetylthiophene (30 g), and the oxygen pressure was at 32 psi (i.e., 4.1 atm)

The results of Experiments 3.1, 3.2, 3.3, and 3.4 are presented below in Table 1. Using the process procedure described in Experiment 2.2 of Example 2 the decreased reaction rate was observed in Experiment 3.2 on a two-fold increased reaction scale, compared to the one in Experiment 3.1. The reduced efficiency of oxidation was consistent with the decreased oxygen partial pressure resulted from the byproduct gas accumulation (e.g., $CO_2$) in the pressure tube. In Experiment 3.3, the reaction mixture in the pressure tube was purged every hour and refilled with fresh oxygen, the reaction rate was observed to improve compared to Experiment 3.2 without purging. However, the decreased reaction rate due to the byproduct gas accumulation was not fully addressed using the process procedure of Experiment 2.2 of Example 2 with periodically purging. By using the process procedure described in Experiment 2.3 of Example 2, the pressure reactor containing the reaction mixture was continuously purged and replaced with a fresh, oxygen-rich gas source. A high rate of reaction was consistently maintained at a lower oxygen pressure on a 6-fold increased scale, presented in Experiment 3.4.

acetic anhydride were added via the additional funnel to the initial mixture. The reaction temperature was maintained at approximately 121° C. to 124° C. and the oxygen pressure was maintained at about 32 psi. The amount of acetic anhydride varied from 1.05 or 1.50 equivalent, based on 2-acetylthiophene.

Experiment 4.1

Acetic anhydride (25.5 g, 250 mmol, 1.05 eq.) was used.

Experiment 4.2

Acetic anhydride (36.4 g, 356 mmol, 1.50 eq.) was used.

The RP-HPLC indicated the conversion of 2-acetylthiophene to 2-thiophenecarboxylic acid was 97 area % for Exp. 4.1 and >98.6 area % for Exp. 4.2. The $^1$H NMR data indicated that there was no detectable trace of formic acid present in the final product mixture when 1.50 equivalent of acetic acid was used in Experiment 4.2. In both experiments, the starting material, 2-acetylthiophene was not detected in the final product mixture.

It was confirmed that acetic anhydride assisted the oxidation by removal of formic acid in the reaction mixture; therefore, increased the conversion of 2-acetylthiophene to 2-thiophenecarboxylic acid from about 93 area % (Exp. 3.4) to >98.6 area % (Exp. 4.2).

TABLE 1

Efficiency of Oxidation Affected by Oxygen Pressure, Temperature, and Purging

| Exp. No. | Exp. 3.1 | Exp. 3.2 | Exp. 3.3 | Exp. 3.4 |
|---|---|---|---|---|
| Process Procedure | Exp. 2.2 of Example 2 | Exp. 2.2 of Example 2 | Exp. 2.2 of Example 2 | Exp. 2.3 of Example 2 |
| Vessel | Pressure tube | Pressure tube | Pressure tube | Pressure reactor |
| Catalyst[a] (mol %) | $Co^{2+}$ (3 mol %), $Mn^{2+}$ (3 mol %) | $Co^{2+}$ (3 mol %), $Mn^{2+}$ (3 mol %) | $Co^{2+}$ (3 mol %), $Mn^{2+}$ (3 mol %) | $Co^{2+}$ (3 mol %), $Mn^{2+}$ (3 mol %) |
| Solvent | AcOH | AcOH | AcOH | AcOH |
| $O_2$ Pressure (psi) | 60 | 60 | 70 | 32 |
| $O_2$ Purging | No | No | Yes[b] | Yes[c] |
| Scale (g) | 5 | 10 | 10 | 30 |
| T (° C.) | 125 | 125 | 115 | 120 |
| Reaction time (h) | 3 | 3 | 5 | 4 |
| AcT[d]:TCA[e] by RP-HPLC (area %) | 54:46 | 61:39 | 12:88 | 7:93 |

[a]The catalysts were introduced into the reaction mixture as $Co(OAc)_2 \cdot 4H_2O$ and $Mn(OAc)_2 \cdot 4H_2O$.
[b]Oxygen purging every hour.
[c]Continuous oxygen purging.
[d]AcT is 2-acetylthiophene.
[e]TCA is 2-thiophenecarboxylic acid.

Example 4

Efficiency of Oxidation from 2-Acetylthiophene to 2-Thiophenecarboxylic Acid (with an Anhydride)

Experiment 2.4 of Example 2 was repeated with acetic anhydride added. In these experiments, $Co(OAc)_2 \cdot 4H_2O$ (3 mol %), $Mn(OAc)_2 \cdot 4H_2O$ (3 mol %), and acetic acid (approximately 180 mL) were mixed altogether in the pressure reactor and placed under oxygen (i.e., 32 psi) without 2-acetylthiophene. After heating to about 90° C., 2-acetylthiophene (30 g, 238 mmol) in acetic acid (30 mL) with

Example 5

Preparation of 2-Thiophenecarboxylic Acid from Thiophene

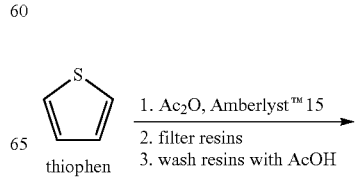

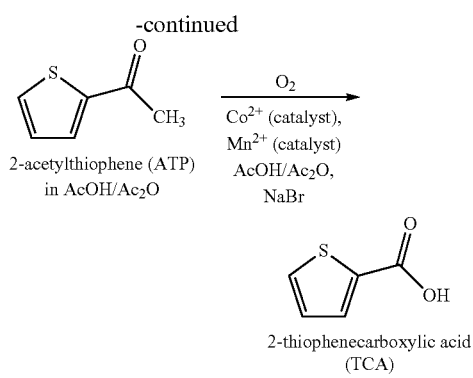

2-acetylthiophene (ATP) in AcOH/Ac$_2$O 2-thiophenecarboxylic acid (TCA)

Step-1: Preparation of a Solution of 2-Acetylthiophene in AcOH/Ac$_2$O

Experiment 5.1

Acetic anhydride (284 mL, 3.0 mol, 2.0 eq.) and AMBERLYST™ 15 (in an acid form) resins (16.0 g, 75.2 mmol, 0.05 eq.) were charged into a 1-L jacketed reactor with mechanical stirring. The reaction mixture was heated to 30° C. The thiophene (120 mL, 1.50 mol) was added dropwise over a period of 20 minutes. The reaction temperature was raised to 35° C. RP-HPLC indicated that the conversion of from thiophene to 2-acetylthiophene was about 87% after 3 hours. The reaction temperature was raised again to 40° C. and the conversion reached 99% after 1 hour. After cooling, the product mixture was filtered into a tared flask. The resins were washed with acetic acid (86 mL, 1.5 mol, 1.0 eq.), and the wash eluent was combined with the filtered product mixture to form a liquid medium for the next oxidation step. RP-HPLC analysis indicated that the liquid medium had the following composition: 2-acetylthiophene (34.8 w.t. %, 90.6% yield), acetic acid (33.8 w.t. %), acetic anhydride (30.6 w.t. %), unreacted thiophene (0.32 w.t. %), and aldol condensation dimer (0.35 w.t. %).

Experiment 5.2

Experiment 5.1 was repeated except that the reaction temperature was raised to 40° C. after completion of the thiophene addition. RP-HPLC indicated the conversion reached 99% after 4 hours. RP-HPLC analysis indicated that the liquid medium had the following composition: 2-acetylthiophene (36.6 w.t. %, 96.6% yield), acetic acid (33.8 w.t. %), acetic anhydride (29.0 w.t. %), unreacted thiophene (0.16 w.t. %), and aldol condensation dimer (0.48 w.t. %).

Step-2: Oxidation of 2-Acetylthiophene in AcOH/Ac$_2$O/NaBr

Experiment 5.3

The liquid medium from Experiment 5.1 was subjected for oxidation using the procedure described in Experiment 2.4 of Example 2. In this experiment, Co(OAc)$_2$.4H$_2$O (2.5 mol %), Mn(OAc)$_2$.4H$_2$O (2.5 mol %), NaBr (2.5 mol %), and acetic acid (approximately 176 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (29.1 g), and acetic anhydride (26.6 g, 260 mmol, 1.1 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 45 minutes. After additional 2 hours, the reaction mixture was cooled for further isolation process. RP-HPLC indicated that the conversion of 2-acetylthiophene to 2-thiophenecarboxylic acid was quantitative. However, 5-bromothiophene-2-carboxylic acid as the by-product was produced at the level of >1000 ppm.

Experiment 5.4

The liquid medium from Experiment 5.2 was subjected for oxidation using the procedure described in Experiment 2.4 of Example 2. In this experiment, Co(OAc)$_2$.4H$_2$O (2.5 mol %), Mn(OAc)$_2$.4H$_2$O (2.5 mol %), NaBr (2.5 mol %), and acetic acid (approximately 175 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (28.2 g), and acetic anhydride (23.8 g, 233 mmol, 1.0 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 40 minutes. After additional 2 hours, the reaction mixture was cooled for further isolation process. RP-HPLC indicated that the conversion of 2-acetylthiophene to 2-thiophenecarboxylic acid was quantitative with 5-bromothiophene-2-carboxylic acid as of 2.5 area %.

Experiment 5.5

The liquid medium from Experiment 5.2 was subjected for oxidation using the procedure described in Experiment 2.4 of Example 2. In this experiment, Co(OAc)$_2$.4H$_2$O (2.0 mol %), Mn(OAc)$_2$.4H$_2$O (2.0 mol %), NaBr (2.0 mol %), and acetic acid (approximately 175 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (28.2 g), and acetic anhydride (23.8 g, 233 mmol, 1.0 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 20 minutes. After additional 2 hours, the reaction mixture was cooled for further isolation process. RP-HPLC indicated that the conversion of 2-acetylthiophene to 2-thiophenecarboxylic acid was quantitative with 5-bromothiophene-2-carboxylic acid as of 2.2 area %.

Experiment 5.6

The liquid medium from Experiment 5.2 was subjected for oxidation using the procedure described in Experiment 2.4 of Example 2. In this experiment, Co(OAc)$_2$.4H$_2$O (2.5 mol %), Mn(OAc)$_2$.4H$_2$O (2.5 mol %), NaBr (0.12 mol %), and acetic acid (approximately 175 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (28.2 g), and acetic anhydride (23.8 g, 233 mmol, 1.0 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 20 minutes. After additional 2 hours, the reaction mixture was cooled for further isolation process. RP-HPLC indicated that the conversion of 2-acetylthiophene to 2-thiophenecarboxylic acid was about 99%. By lowing the amount of NaBr, 5-bromothiophene-2-carboxylic acid was produced at the level of <1000 ppm.

Example 6

Oxidation from 2-Acetylthiophene to 2-Thiophenecarboxylic Acid (with Bromide and Zinc Ion)

The liquid medium, prepared by the procedure described in Experiment 5.2, was subjected for oxidation using the procedure described in Experiment 2.4 of Example 2. In this experiment, $Co(OAc)_2 \cdot 4H_2O$ (3 mol %), $Mn(OAc)_2 \cdot 4H_2O$ (3 mol %), NaBr (0.12 mol %), $Zn(OAc)_2$ (0.10 mol %), and acetic acid (approximately 175 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (30.9 g), and acetic anhydride (24.9 g, 244 mmol, 1.05 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 40 minutes. After additional 2.5 hours, the reaction mixture was cooled for further isolation process. RP-HPLC indicated that the conversion of 2-acetylthiophene to 2-thiophenecarboxylic acid was about 99.7%.

Example 7

Oxidation from 2-Acetylthiophene to 2-Thiophenecarboxylic Acid (with Chloride)

The liquid medium, prepared by the procedure described in Experiment 5.2, was subjected for oxidation using the procedure described in Experiment 2.4 of Example 2.

Experiment 7.1

$Co(OAc)_2 \cdot 4H_2O$ (2.5 mol %), $Mn(OAc)_2 \cdot 4H_2O$ (2.5 mol %), NaCl (2.5 mol %), and acetic acid (approximately 175 mL) were mixed altogether in the pressure reactor and placed under oxygen (i.e., 32 psi) without 2-acetylthiophene. After heating to about 90° C., the liquid medium comprising 2-acetylthiophene (30.0 g, 238 mmol), acetic acid (29.2 g), and acetic anhydride (24.2 g, 237 mmol, 1.0 eq.) was added via the additional funnel to the initial mixture. The reaction temperature was then maintained at approximately 121° C. to 125° C. and the oxygen pressure was maintained at about 32 psi. After 2 hours, another portion of acetic anhydride (12.2 g, 119 mmol, 0.5 eq.) was added gradually over 35 minutes. After an additional 2.5 hours, the reaction mixture was cooled for further isolation process. RP-HPLC indicated that the conversion of 2-acetylthiophene to 2-thiophenecarboxylic acid was quantitative.

Experiment 7.2

Experiment 7.1 was repeated except that $Co(OAc)_2 \cdot 4H_2O$ (2.0 mol %), $Mn(OAc)_2 \cdot 4H_2O$ (2.0 mol %), and NaCl (2.0 mol %) were used. RP-HPLC indicated that the conversion of 2-acetylthiophene to 2-thiophenecarboxylic acid was about 99.7%.

Experiment 7.3

Experiment 7.2 was repeated except that KCl (2.0 mol %) were used in the place of NaCl. RP-HPLC indicated that the conversion of 2-acetylthiophene to 2-thiophenecarboxylic acid was about 99.6%.

Example 8

Oxidation from 2-Acetylthiophene to 2-Thiophenecarboxylic Acid (with Nitrate)

A liquid medium, prepared by the procedure described in Experiment 5.2, was subjected for oxidation using the procedure described in Experiment 2.4 of Example 2. In this experiment, $Co(OAc)_2 \cdot 4H_2O$ (2.5 mol %), $Mn(OAc)_2 \cdot 4H_2O$ (2.5 mol %), $NaNO_3$ (2.5 mol %), and acetic acid (approximately 175 mL) were mixed altogether in the pressure reactor and placed under oxygen (i.e., 32 psi) without 2-acetylthiophene. After heating to about 80° C., the liquid medium comprising 2-acetylthiophene (30.0 g, 238 mmol), acetic acid (29.2 g), and acetic anhydride (24.2 g, 237 mmol, 1.0 eq.) was added via the additional funnel to the initial mixture. The reaction temperature was then maintained at approximately 111° C. to 115° C. and the oxygen pressure was maintained at about 32 psi. After 2 hours, another portion of acetic anhydride (12.2 g, 119 mmol, 0.5 eq.) was added gradually over 20 minutes. The reaction temperature was then gradually increased to approximately 120° C. over 45 minutes, and then maintained at approximately 120° C. After an additional 2 hours, the reaction mixture was cooled for further isolation process. RP-HPLC indicated that the conversion of 2-acetylthiophene to 2-thiophenecarboxylic acid was >99%. 2-Thiopheneglyoxal diacetate was detected as a side product and was present in the product mixture in about 1 area %.

Example 9

Preparation of 2-Thiophenecarboxylic Acid from 2-Thiophenecarboxaldehyde Via Oxidation

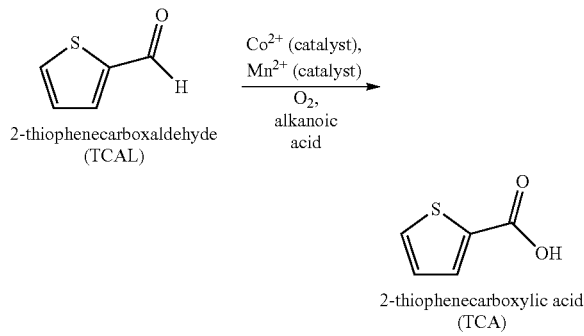

The following are general procedures for the preparation of 2-thiophenecarboxylic acid from 2-thiophenecarboxaldehyde by oxidation. The transition metal ion catalysts (e.g., a salt form, an amount, and a ratio of $Co^{2+}$ and $Mn^{2+}$), the organic solvent of the reaction (e.g., a $C_2$-$C_6$ alkanoic acid), the oxygen pressure, and the reaction temperature can vary during the process of the preparation. The following Experiments 9.2, 9.3, and 9.4 are representative procedures with several variable parameters.

Experiment 9.2: Oxidation Using Catalysts of $Co(OAc)_2$ and $Mn(OAc)_2$ in Acetic Acid Under Oxygen 2-Thiophenecarboxaldehyde (5.0 g, 44.6 mmol) was dissolved in acetic acid (20 mL) in a pressure tube. The transition metal ion catalysts, $Co(OAc)_2 \cdot 4H_2O$ (336 mg, 1.35 mmol) and $Mn(OAc)_2 \cdot 4H_2O$ (33 mg, 0.13 mmol), were added to the solution of 2-thiophenecarboxaldehyde, and the resulting solution color turned to red. Subsequently, an aqueous solution of HBr (48%, 300 mg, 1.8 mmol) was added and the color of the resulting solution changed from previous red to blue. The pressure tube containing the reaction mixture was evacuated under a vacuum, and then filled with oxygen and the oxygen pressure was maintained at 65 psi (i.e., 4.4 atm). The resulting mixture in the pressure tube was heated to 120° C. under oxygen at 65 psi. After heating at 120° C. for 1.5 hours, the oxygen uptake was observed to cease. After cooling to room temperature, the reaction mixture was filtered to remove the formed solids. The solvent was removed by evaporation, and the resulting solids were partitioned between water and ethyl acetate. The organic layer was treated with active carbon, filtered, and then dried over anhydrous magnesium sulfate. After concentration, the title compound was obtained as a solid. The RP-HPLC analysis showed that the obtained material was 2-thiophenecarboxylic acid with a purity of >94 area %.

Experiment 9.3: Oxidation Using Catalysts of $Co(OAc)_2$ and $Mn(OAc)_2$ in Acetic Acid Under Oxygen (with Continuous Purging)

A pressure reactor was equipped with a feed inlet, an oxygen inlet, an oxygen sparger, a thermocouple, a mechanical stirrer, a condenser, and a manifold containing a pressure gauge, pressure relief valve, and rupture disc. A solution of 2-thiophenecarboxaldehyde (30.0 g, 267.5 mmol), dissolved in acetic acid (240 mL), was placed in the pressure reactor. The transition metal ion catalysts, $Co(OAc)_2 \cdot 4H_2O$ (2000 mg, 8.0 mmol) and $Mn(OAc)_2 \cdot 4H_2O$ (197 mg, 0.8 mmol), were added to the solution of 2-thiophenecarboxaldehyde. Subsequently, an aqueous solution of HBr (48%, 1800 mg, 10.8 mmol) was added. The pressure reactor containing the reaction mixture was evacuated under a vacuum, and then filled with oxygen and the oxygen pressure was maintained at 32 psi (i.e., 2.2 atm). The resulting mixture in the pressure reactor was heated to 120° C. under oxygen at 32 psi. The oxygen uptake was observed to start at approximately 100° C., and the reaction mixture in the pressure reactor was purged and refilled with fresh oxygen continuously. After rapid uptake of oxygen, the reaction mixture started self-heating and cooling may be necessary to maintain the desired reaction temperature. After heating at approximately 120° C. for 1.5 hours, the oxygen uptake was observed to cease. After cooling to room temperature, the reaction mixture was filtered to remove the formed solids. The solvent was removed by evaporation, and the resulting solids were partitioned between water (100 mL) and ethyl acetate (400 mL). The organic layer was washed with water and saturated NaCl solution, and then dried over anhydrous magnesium sulfate. The organic solution was treated with active carbon and filtered to provide a red solution. After concentration, the title compound was obtained as a tan-colored solid (34 g). Both RP-HPLC and GC-FID analyses showed that the obtained material was 2-thiophenecarboxylic acid with a purity of >99 area %.

Experiment 9.4: Oxidation Using Catalysts of $Co(OAc)_2$ and $Mn(OAc)_2$ in Acetic Acid Under Oxygen (with Continuous Purging) with/without an Initiation of the Reaction A pressure reactor was equipped with a feed inlet, an oxygen inlet, an oxygen sparger, a thermocouple, a mechanical stirrer, a condenser, and a manifold containing a pressure gauge, pressure relief valve, and rupture disc. A solution of 2-thiophenecarboxaldehyde (4.0 g, 35.7 mmol), dissolved in acetic acid (180 mL), was placed in the pressure reactor. The transition metal ion catalysts, $Co(OAc)_2 \cdot 4H_2O$ (98.0%, 1500 mg, 5.9 mmol) and $Mn(OAc)_2 \cdot 4H_2O$ (99.0%, 148 mg, 0.6 mmol), were added to the solution of 2-thiophenecarboxaldehyde. The residues of the catalysts were rinsed with acetic acid (30 mL) and added to the reaction mixture. Subsequently, an aqueous solution of HBr (48%, 1340 mg, 8.0 mmol) was added. The feed inlet was connected with an additional funnel charged with the remaining 2-thiophenecarboxaldehyde (26.0 g, 231.8 mmol) in acetic acid (30 mL). The pressure reactor containing the reaction mixture was evacuated under a vacuum, and then filled with oxygen and the oxygen pressure was maintained at 32 psi (i.e., 2.2 atm). After the reaction was initiated, the aldehyde in the additional funnel was added into the reaction mixture containing catalysts at a temperature of 75-100° C. over a period of 30-45 minutes; during which, the oxygen pressure was maintained at a range of 30-35 psig. In general, the reaction was sufficiently exothermic during the 2-thiophenecarboxaldehyde addition to maintain the reaction temperature between 100° C. and 120° C., even when the heating source was removed. The reaction was completed in an hour after heating at 120° C. The reaction mixture in the pressure reactor was purged and refilled with fresh oxygen continuously during the reaction.

The initiation of the reaction, described above, is optional for a large scale process. Alternatively, the transition metal ion catalysts, an aqueous solution of HBr, and acetic acid can be mixed altogether in the pressure reactor and placed under oxygen without 2-thiophenecarboxaldehyde. After heating, 2-thiophenecarboxaldehyde can be added via the additional funnel to the initial mixture at a desired temperature and under the desired oxygen pressure.

After cooling to room temperature, the reaction mixture was filtered to remove the formed solids. The solvent was removed by evaporation, and the resulting solids were subjected to extraction for isolation of the desired product of 2-thiophenecarboxylic acid.

Example 10

Efficiency of Oxidation from 2-Thiophenecarboxaldehyde to 2-Thiophenecarboxylic Acid (Oxygen Pressure and Purging Effect)

Experiment 10.1

Experiment 9.2 of Example 9 was repeated.

Experiment 10.2

Experiment 9.2 of Example 9 was repeated on a scale of 2-thiophenecarboxaldehyde (10 g), and the oxygen pressure was at 70 psi (i.e., 4.8 atm).

Experiment 10.3

Experiment 9.3 of Example 9 was repeated

Experiment 10.4

Experiment 9.3 of Example 9 was repeated.

The results of Experiments 10.1, 10.2, 10.3, and 10.4 are presented below in Table 2. There was no significant difference of the reaction rate was observed by increasing the oxygen pressure (e.g., from 65 psi to 70 psi). A similar reaction rate was achieved on a two-fold increased reaction scale, since the byproduct gas accumulation (e.g., $CO_2$) was not involved in this conversion reaction of from 2-thiophenecarboxaldehyde to 2-thiophenecarboxylic acid. However, the process procedure described in Experiment 9.3 of Example 9 was preferred under a lower oxygen pressure, where the pressure reactor containing the reaction mixture was continuously purged and replaced with a fresh, oxygen-rich gas source. A high rate of reaction was consistently maintained at a lower oxygen pressure on a 6-fold increased scale, presented in Experiments 10.3 and 10.4.

Example 11

Efficiency of Oxidation from 2-Thiophenecarboxaldehyde to 2-Thiophenecarboxylic Acid (Bromide Effect)

In the following experiments, $Co(OAc)_2 \cdot 4H_2O$ (3 mol %) and $Mn(OAc)_2 \cdot 4H_2O$ (0.3 mol %) were used. Bromide source was an aqueous solution of HBr (4 mol %), NaBr (4 mol %), or none (0 mol %).

Experiment 11.1

Experiment 9.4 of Example 9 was repeated with the amounts of transition metal catalysts mentioned above. In this experiment, an aqueous solution of HBr (4 mol %) was used. The reaction was initiated with 2-thiophenecarboxaldehyde (2 g), and the remaining aldehyde (28 g) was added during the reaction.

Experiment 11.2

Experiment 9.4 of Example 9 was repeated with the amounts of transition metal catalysts mentioned above. In this experiment, NaBr (4 mol %) was used.

Experiment 11.3

Experiment 9.4 of Example 9 was repeated with the amounts of transition metal catalysts mentioned above. In this experiment, the oxidation was conducted in the absence of either HBr or NaBr.

The results of Experiments 11.1, 11.2, and 11.3 are presented below in Table 3. Sodium bromide, as an alternative bromide source in the place of HBr, achieved the same efficiency of the oxidation reaction. In the absence of bromide source (e.g., HBr or NaBr), the oxidation reaction was incomplete under the current conditions.

TABLE 2

| Efficiency of Oxidation Affected by Oxygen Pressure and Purging | | | | |
|---|---|---|---|---|
| Exp. No. | Exp. 10.1 | Exp. 10.2 | Exp. 10.3 | Exp. 10.4 |
| Process Procedure | Exp. 9.2 of Example 9 | Exp. 9.2 of Example 9 | Exp. 9.3 of Example 9 | Exp. 9.3 of Example 9 |
| Vessel | Pressure tube | Pressure tube | Pressure reactor | Pressure reactor |
| Catalyst[a] (mol %) | $Co^{2+}$ (3 mol %), $Mn^{2+}$ (0.3 mol %) | $Co^{2+}$ (3 mol %), $Mn^{2+}$ (0.3 mol %) | $Co^{2+}$ (3 mol %), $Mn^{2+}$ (0.3 mol %) | $Co^{2+}$ (3 mol %), $Mn^{2+}$ (0.3 mol %) |
| 48% HBr (mol %) | 4.0 | 4.0 | 4.0 | 4.0 |
| Solvent | AcOH | AcOH | AcOH | AcOH |
| $O_2$ Pressure (psi) | 65 | 70 | 32 | 32 |
| $O_2$ Purging | No | No | Yes[b] | Yes[b] |
| Scale (g) | 5 | 10 | 30 | 30 |
| T (° C.) | 120 | 120 | 120 | 120 |
| Reaction time (h) | 1.5 | 1.5 | 1.5 | 2 |
| TCAL[c]:TCA[d] by RP-HPLC (area %) | 1:94 | 1:98 | 0.5:98 | <0.2:>99 |

[a]The catalysts were introduced into the reaction mixture as $Co(OAc)_2 \cdot 4H_2O$ and $Mn(OAc)_2 \cdot 4H_2O$.
[b]Continuous oxygen purging.
[c]TCAL is 2-thiophenecarboxaldehyde.
[d]TCA is 2-thiophenecarboxylic acid.

TABLE 3

Efficiency of Oxidation Affected by Bromide Source

| Exp. No. | Exp. 11.1 | Exp. 11.2 | Exp. 11.3 |
|---|---|---|---|
| Catalyst[a] (mol %) | $Co^{2+}$ (3 mol %), $Mn^{2+}$ (0.3 mol %) | $Co^{2+}$ (3 mol %), $Mn^{2+}$ (0.3 mol %) | $Co^{2+}$ (3 mol %), $Mn^{2+}$ (0.3 mol %) |
| Bromide source (mol %) | HBr (4 mol %) | NaBr (4 mol %) | None (0 mol %) |
| Scale (g) | 30 | 30 | 30 |
| TCAL[b] Conc. (M) | 1.1 | 1.1 | 1.1 |
| $O_2$ Pressure (psi) | 32 | 32 | 32 |
| T (° C.) | 99-106 | 100-105 | 120-128 |
| Yield (%) | 98.2[c] | 96.3[d] | 47.4[d] |

[a]The catalysts were introduced into the reaction mixture as $Co(OAc)_2 \cdot 4H_2O$ and $Mn(OAc)_2 \cdot 4H_2O$.
[b]TCAL is 2-thiophenecarboxaldehyde.
[c]GC-FID analysis of the crude material of 2-thiophenecarboxylic acid after removal of acetic acid.
[d]RP-HPLC analysis of the crude material of 2-thiophenecarboxylic acid in acetic acid.

Example 12

Efficiency of Oxidation from 2-Thiophenecarboxaldehyde to 2-Thiophenecarboxylic Acid (Amounts of Catalysts and Bromide)

In the following experiments, Experiment 9.4 of Example 9 was repeated with different amounts of transition metal catalysts and HBr (or NaBr). The reduction of catalysts and HBr (or NaBr) was explored to achieve the same efficiency of oxidation.

Experiment 12.1

In this experiment, $Co(OAc)_2 \cdot 4H_2O$ (3 mol %), Mn $(OAc)_2 \cdot 4H_2O$ (0.3 mol %), and an aqueous solution of HBr (4 mol %) were used. The reaction was initiated with 2-thiophenecarboxaldehyde (2 g), and the remaining aldehyde (28 g) was added during the reaction.

Experiment 12.2

Experiment 9.4 of Example 9 was presented.

Experiment 12.3

Experiment 9.4 of Example 9 was repeated with reduced amounts of transition metal catalysts and HBr at a doubled reaction concentration. In this experiment, $Co(OAc)_2 \cdot 4H_2O$ (0.75 mol %), $Mn(OAc)_2 \cdot 4H_2O$ (0.075 mol %), and an aqueous solution of HBr (1 mol %) were used and the initial reaction concentration of 2-thiophenecarboxaldehyde was at 2.2 M.

Experiment 12.4

Experiment 9.4 of Example 9 was repeated on a scale of 2-thiophenecarboxaldehyde (90 g), with further reduced amounts of transition metal catalysts and HBr and at a higher reaction concentration. In this experiment, $Co(OAc)_2 \cdot 4H_2O$ (0.25 mol %), $Mn(OAc)_2 \cdot 4H_2O$ (0.025 mol %), and NaBr (0.33 mol %) were used and the initial reaction concentration of 2-thiophenecarboxaldehyde was at 3.1 M.

The results of Experiments 12.1, 12.2, 12.3, and 12.4 are presented below in Table 4. The experiment 12.3 provided a comparable yield, when the amounts of catalysts and HBr were reduced by 4-fold. Therefore, the cost savings of catalysts can be achieved for a large scale process. By further reducing the catalysts and bromide (NaBr), the oxidation reaction in Experiment 12.4 was incomplete under the current conditions.

TABLE 4

Efficiency of Oxidation Affected by the Amount of Catalysts and Bromide

| Exp. No. | Exp. 12.1 | Exp. 12.2 | Exp. 12.3 | Exp. 12.3 |
|---|---|---|---|---|
| Catalyst[a] (mol %) | $Co^{2+}$ (3 mol %), $Mn^{2+}$ (0.3 mol %) | $Co^{2+}$ (2.25 mol %), $Mn^{2+}$ (0.225 mol %) | $Co^{2+}$ (0.75 mol %), $Mn^{2+}$ (0.075 mol %) | $Co^{2+}$ (0.25 mol %), $Mn^{2+}$ (0.025 mol %) |
| 48% HBr (mol %) | 4.0 | 3.0 | 1.0 | — |
| NaBr (mol %) | — | — | — | 0.33 |
| Scale (g) | 30 | 30 | 30 | 90 |
| TCAL[b] Conc. (M) | 1.1 | 1.1 | 2.2 | 3.1 |
| T (° C.) | 99-106 | 100-105 | 115-120 | 100-120 |
| Yield (%) | 98.2[c] | 100.0[d] | 94.4[e] | 47.3[e] |

[a]The catalysts were introduced into the reaction mixture as $Co(OAc)_2 \cdot 4H_2O$ and $Mn(OAc)_2 \cdot 4H_2O$.
[b]TCAL is 2-thiophenecarboxaldehyde.
[c]GC-FID analysis of the crude material of 2-thiophenecarboxylic acid after removal of acetic acid.
[d]RP-HPLC analysis of the crude material of 2-thiophenecarboxylic acid after removal of acetic acid.
[e]RP-HPLC analysis of the crude material of 2-thiophenecarboxylic acid in acetic acid.

Example 13

Preparation of 2-Thiophenecarboxylic Acid for Use in the Chlorinating Step

A suitable solvent, for example, butyl acetate, butyl ether, or xylenes, was explored for extraction of 2-thiophenecarboxylic acid and azeotropic distillation of removing water of the extract comprising 2-thiophenecarboxylic acid.

Experiment 13.1

The reaction mixture, prepared from Experiment 9.4 of Example 9 was cooled to room temperature and then filtered to remove the formed solids. The solvent was removed by evaporation, and the resulting solids were dissolved in butyl acetate (115 mL) at 60° C. All washes and extractions were conducted with stirring at 60° C. for 15 minutes, settling for 5 minutes, and followed by separation. The organic phase was first washed with water (50 mL), followed by washed with an aqueous HCl solution (0.37 M, 53 mL). The combined hot organic layers were filtered to remove any visible solids. The first aqueous wash solution was extracted with butyl acetate (50 mL), and the second aqueous wash solution was extracted with butyl acetate (50 mL). The combined organic layers were subjected for azeotropic distillation for removal of solvent to provide dehydrated 2-thiophenecarboxylic acid. RP-HPLC analysis determined the 2-thiophenecarboxylic acid as a solution of butyl acetate was obtained in 93.5% with a purity of >99 area %. The concentration of 2-thiophenecarboxylic acid in butyl acetate was determined to be 23.8 wt. %.

The above-mentioned solution of 2-thiophenecarboxylic acid in butyl acetate was used directly for the chlorinating step to prepare 2-thiophenecarbonyl chloride (TCC).

Experiment 13.2

The reaction mixture, prepared from Experiment 5.5 of Example 5, was cooled to about 50° C. and transferred to a round-bottom flask. The solvent was removed by evaporation, and the resulting solids were mixed with butyl acetate (200 g) and 1 N aq. HCl (50 mL) and stirred vigorously. After separating the layers in a separatory funnel, the aqueous layer was extracted with additional butyl acetate (2×50 mL). The combined organic layers were subjected for solvent removal to provide the crude product as a tan solid (31.77 g, 99%). $^1$H NMR determined the crude product had the following composition: 2-thiophenecarboxylic acid (95%), acetic acid (1.9%), acetic anhydride (0.2%), and butyl acetate (2.5%).

Experiment 13.3

The reaction mixture, prepared from Experiment 5.4 of Example 5, was cooled to about 50° C. and transferred to a round-bottom flask. The mixture was then heated to 60° C. under nitrogen with stirring while oxalic acid.2H$_2$O (1.90 g, 1.25 eq.) was added. The temperature of the resulting mixture rose up to 68° C. The warm mixture was filtered; the solid were washed with acetic acid (60 to 70 mL) to provide a dark brown filtrate (353.11 g). After concentration, the obtained amber solid (39.00 g) was mixed with butyl acetate (200 g) and water (50 g) in a flask with stirring, followed by addition of aqueous HCl solution (12 N, 1 mL). The stirring was continued for a few minutes, and the layers were separated in a separatory funnel. The aqueous layer was extracted with butyl acetate (2×50 g). During the final extraction, additional aqueous HCl solution (12 N, 2 mL) was added to break up the newly formed insoluble layer. All butyl acetate extracts were combined and concentrated to provide the crude product as a tan solid (30.50 g, 99%). $^1$NMR determined the crude product had the following composition: 2-thiophenecarboxylic acid (98.5%), acetic acid (0.4%), acetic anhydride (0.1%), and butyl acetate (1.1%). Metal ICP/MS analyses of the crude product filtrate (after treatment with oxalic acid) indicated that Co and Mn ions were present in the filtrate in an average of 42 ppm and 18.1 ppm, respectively.

Example 14

Conversion of 2-Thiophenecarboxylic Acid to 2-Thiophenecarbonyl Chloride

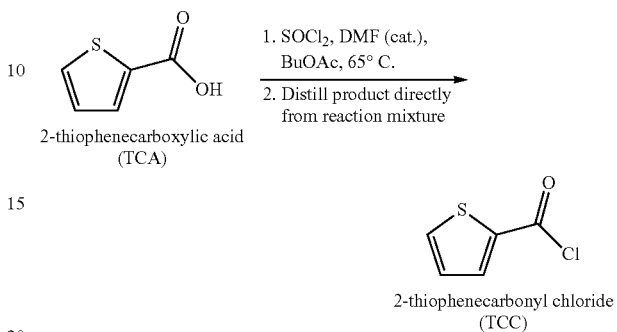

Experiment 14.1

In this experiment, the 2-thiophenecarboxylic acid was prepared by Experiment 12.1 of Example 12; the resulting solution of 2-thiophenecarboxylic acid in butyl acetate (24.8 wt. %) was prepared by Experiment 13.1 of Example 13, except that the aqueous HCl wash was omitted.

The solution of 2-thiophenecarboxylic acid in butyl acetate (24.8 wt. %, 47.5 g, 91.9 mmol) was diluted with butyl acetate (40 mL). A catalytic amount of dimethylformamide (DMF) (0.3 mL, 0.043 eq.) was added followed by a slow addition of thionyl chloride (SOCl$_2$) (7.75 mL, 1.15 eq.). During the addition, gases such as sulfur dioxide (SO$_2$) and hydrogen chloride (HCl) were released. The resulting mixture was heated at 65° C. for 2.5 hours after completion of the addition, followed by cooling to ambient temperature. By vacuum distillation (short path), butyl acetate was distilled from the mixture first at a vapor temperature of approximately 75° C. (at approximately 125 mmHg) and then at a vapor temperature of approximately 65° C. (at approximately 60 mmHg). The remaining mixture was cooled to room temperature and switched to a higher vacuum. Distillation (short path, approximately 4 mmHg) at a vapor temperature of approximately 60° C. afforded 2-thiophenecarbonyl chloride as a clear pale yellow oil (8.7 g, 63%). GC-FID confirmed that the obtained material was 2-thiophenecarbonyl chloride with a purity of >98 area %.

Experiment 14.2

In this experiment, the 2-thiophenecarboxylic acid was the combined solids from Experiments 13.2 and 13.3 of Example 13.

The combined solids of 2-thiophenecarboxylic acid (63.1 g, 493 mmol) was dissolved in ethyl acetate (208 g) in a 3-neck round-bottom flask equipped with a thermocouple, a reflux condenser, and an additional funnel and the system was purged with nitrogen. The reflux condenser outlet was connected to a chilled receiver containing aq. NaOH (20%, 250 g). A catalytic amount of dimethylformamide (DMF) (0.2 mL, 0.005 eq.) was added and the resulting reaction mixture was heated to 65° C. with stirring, followed by a slow addition of thionyl chloride (67.2, 565 mmol, 1.15 eq.). During the addition, gases such as sulfur dioxide (SO$_2$) and hydrogen chloride (HCl) were released and the reaction temperature dropped to about 58° C. The reaction completed in 2.5 hours with no detectable unreacted 2-thiophenecarboxylic acid by GC/MS.

After cooling, the flask was fitted with a distillation head and 4-Methoxyphenol (8.9 mg) was added as a stabilizer during the distillation. By vacuum distillation (short path), ethyl acetate and thionyl chloride were distilled from the mixture first under a lower vacuum (approximately 60 to 125 mmHg). The remaining mixture was cooled to room temperature and switched to a higher vacuum. Distillation (short path, approximately 4 mmHg) at a vapor temperature of approximately 63° C. afforded 2-thiophenecarbonyl chloride as a clear pale yellow oil (56.5 g, 81%). GC-FID confirmed that the obtained material was 2-thiophenecarbonyl chloride with a purity of >98 area %.

2-Thiophenecarbonyl chloride was produced by the processes described above. The processes included: 1) acylation of thiophene; 2) oxidation of 2-acetylthiophene; 3) isolation of 2-thiophenecarboxylic acid; 4) chlorination of 2-thiophenecarboxylic acid; 5) distillation of 2-thiophenecarbonyl chloride. The overall yield for the entire process (5 steps) from thiophene to 2-thiophenecarbonyl chloride was in about 78%.

Example 15

Efficiency of Oxidation from 2-Acetylthiophene to 2-Thiophenecarboxylic Acid (with a Co-Reductant or a Promoter)

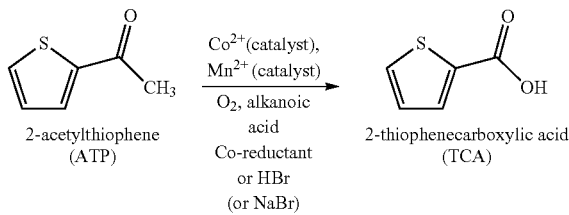

2-acetylthiophene (ATP)

$Co^{2+}$(catalyst), $Mn^{2+}$ (catalyst)
$O_2$, alkanoic acid
Co-reductant or HBr (or NaBr)

2-thiophenecarboxylic acid (TCA)

The following experiments are general procedures for the preparation of 2-thiophenecarboxylic acid from 2-acetylthiophene by oxidation in the presence of a co-reductant (as described in detail above) or HBr (or NaBr). The transition metal ion catalysts (e.g., a salt form, an amount, and a ratio of $Co^{2+}$ and $Mn^{2+}$), the organic solvent of the reaction (e.g., a $C_2$-$C_6$ alkanoic acid), the co-reductant (e.g., lower alkyl aldehydes or dialkyl ketones), the promoter (e.g., HBr or NaBr), the oxygen pressure, and the reaction temperature can vary during the process of the preparation. The following Experiments 15.1, 15.2, and 15.3 are representative procedures with several variable parameters.

Experiment 15.1: Oxidation Using Catalysts of $Co(OAc)_2$ and $Mn(OAc)_2$ in Acetic Acid in the Presence of a Co-Reductant Under Oxygen The procedure in Experiment 2.3 of Example 2 is repeated, except that a solution of a co-reductant in acetic acid (10%) is fed into the reaction mixture at a rate of 3 mL/h during the oxidation. Alternatively, the co-reductant can be added into the reaction mixture intermittently during the oxidation or towards the end of the oxidation. The above-mentioned co-feeding of the co-reductant can be applied to the procedure in Experiment 2.4 of Example 2 in which 2-acetylthiophene is added during the reaction.

Experiment 15.2: Oxidation Using Catalyst of $Co(OAc)_2$ and $Mn(OAc)_2$ in Acetic Acid in the Presence of Bromide Under Oxygen The procedure in Experiment 2.3 of Example 2 is repeated, except that an aqueous solution of HBr (48%, 1800 mg, 10.8 mmol) is added into the reaction mixture before the pressure reactor is evacuated under a vacuum and filled with oxygen. Alternatively, NaBr is used in the place of HBr. The above-mentioned addition of HBr (or NaBr) can be applied to the procedure in Experiment 2.4 of Example 2 in which 2-acetylthiophene is added during the reaction.

Experiment 15.3: Oxidation Using Catalyst of $Co(OAc)_2$ and $Mn(OAc)_2$ in Acetic Acid in the Presence of Nitric Acid Under Oxygen The procedure in Experiment 2.3 of Example 2 is repeated, except that nitric acid (0.74 mL, 17.8 mmol) is added into the reaction mixture before the pressure reactor is evacuated under a vacuum and filled with oxygen. The above-mentioned addition of nitric acid can be applied to the procedure in Experiment 2.4 of Example 2 in which 2-acetylthiophene is added during the reaction.

Example 16

Preparation of 2-Thiophenecarboxylic Acid from 2-Acetylthiophene Via Oxidation (with $Mn^{2+}$)

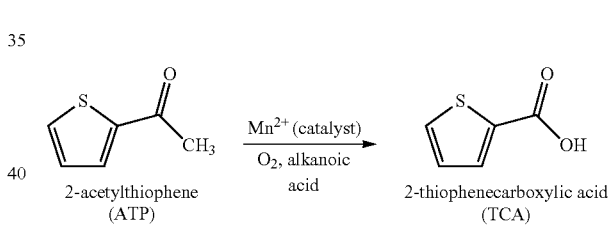

2-acetylthiophene (ATP)

$Mn^{2+}$ (catalyst)
$O_2$, alkanoic acid 2-thiophenecarboxylic acid (TCA)

The following experiments are general procedures for the preparation of 2-thiophenecarboxylic acid from 2-acetylthiophene by oxidation using the transition metal ion catalyst of $Mn^{2+}$. The $Mn^{2+}$ catalyst (e.g., a salt form and an amount), the organic solvent of the reaction (e.g., a $C_2$-$C_6$ alkanoic acid), the co-reductant (e.g., lower alkyl aldehydes or dialkyl ketones), the promoter (e.g., HBr or NaBr), the oxygen pressure, and the reaction temperature can vary during the process of the preparation. The following Experiments 16.1, 16.2, 16.3, and 16.4 are representative procedures.

Experiment 16.1: Oxidation Using Catalyst of $Mn(OAc)_2$ in Acetic Acid Under Oxygen A pressure reactor is equipped with a feed inlet, an oxygen inlet, an oxygen sparger, a thermocouple, a mechanical stirrer, a condenser, and a manifold containing a pressure gauge, pressure relief valve, and rupture disc. A solution of 2-acetylthiophene (30.0 g, 237.4 mmol), dissolved in acetic acid (240 mL), is placed in the pressure reactor. The transition metal ion catalyst, $Mn(OAc)_2 \cdot 4H_2O$ (1.75 g, 7.1 mmol), is added to the solution of 2-acetylthiophene. The pressure reactor containing the reaction mixture is evacuated under a vacuum, and then filled with oxygen and the oxygen pressure is maintained at 32 psi (i.e., 2.2 atm). The resulting mixture in the pressure reactor is heated to from 85° C. to 125° C. under oxygen at 32 psi. During the reaction, the reaction mixture in the pressure reactor is purged and refilled with fresh oxygen continuously. After the oxygen uptake is observed to cease, the cooled reaction mixture is filtered to remove the formed solids. The solvent is removed by evaporation, and the resulting solids are subjected to extraction for isolation of the desired product of 2-thiophenecarboxylic acid.

Alternatively, the transition metal ion catalyst, and acetic acid can be mixed altogether in the pressure reactor and placed under oxygen without 2-acetylthiophene. After heating, 2-acetylthiophene can be added via the additional funnel to the initial mixture at a desired temperature and under the desired oxygen pressure.

Experiment 16.2: Oxidation Using Catalyst of Mn(OAc)$_2$ in Acetic Acid in the Presence of Nitric Acid Under Oxygen The procedure in Experiment 16.1 is repeated, except that nitric acid (0.74 mL, 17.8 mmol) is added into the reaction mixture before the pressure reactor is evacuated under a vacuum and filled with oxygen.

Experiment 16.3: Oxidation Using Catalyst of Mn(OAc)$_2$ in Acetic Acid in the Presence of a Co-Reductant Under Oxygen The procedure in Experiment 16.1 is repeated, except that a solution of a co-reductant in acetic acid (10%) is fed into the reaction mixture at a rate of 3 mL/h during the oxidation. Alternatively, the co-reductant can be added into the reaction mixture intermittently during the oxidation.

Experiment 16.4: Oxidation Using Catalyst of Mn(OAc)$_2$ in Acetic Acid in the Presence of Bromide Anion Under Oxygen The procedure in Experiment 16.1 is repeated, except that an aqueous solution of HBr (48%, 1800 mg, 10.8 mmol) is added into the reaction mixture before the pressure reactor is evacuated under a vacuum and filled with oxygen. Alternatively, NaBr is used in the place of HBr.

Example 17

Preparation of 2-Thiophenecarboxylic Acid from 2-Thiophenecarboxaldehyde Via Oxidation (with Co$^{2+}$)

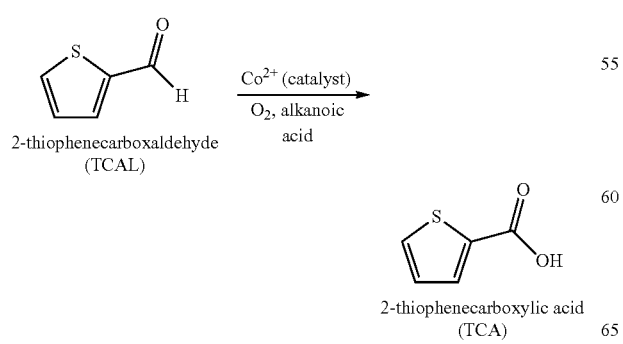

A general procedure is provided as following for the preparation of 2-thiophenecarboxylic acid from 2-thiophenecarboxaldehyde by oxidation using the transition metal ion catalyst of Co$^{2+}$. The Co$^{2+}$ catalyst (e.g., a salt form and an amount), the organic solvent of the reaction (e.g., a C$_2$-C$_6$ alkanoic acid), the oxygen pressure, and the reaction temperature can vary during the process of the preparation.

A pressure reactor is equipped with a feed inlet, an oxygen inlet, an oxygen sparger, a thermocouple, a mechanical stirrer, a condenser, and a manifold containing a pressure gauge, pressure relief valve, and rupture disc. A solution of 2-thiophenecarboxaldehyde (4.0 g, 35.7 mmol), dissolved in acetic acid (180 mL), is placed in the pressure reactor. The transition metal ion catalyst, Co(OAc)$_2$.4H$_2$O (98.0%, 1500 mg, 5.9 mmol), is added to the solution of 2-thiophenecarboxaldehyde. The residues of the catalyst are rinsed with acetic acid (30 mL) and added to the reaction mixture. Subsequently, an aqueous solution of HBr (48%, 1340 mg, 8.0 mmol) is added. The feed inlet is connected with an additional funnel charged with the remaining 2-thiophenecarboxaldehyde (26.0 g, 231.8 mmol) in acetic acid (30 mL). The pressure reactor containing the reaction mixture is evacuated under a vacuum, and then filled with oxygen and the oxygen pressure is maintained at 32 psi (i.e., 2.2 atm). After the reaction is initiated, the aldehyde in the additional funnel is added into the reaction mixture containing catalysts at a temperature of 75-100° C. over a period of 30-45 minutes; during which, the oxygen pressure is maintained at a range of 30-35 psig. The reaction mixture in the pressure reactor is purged and refilled with fresh oxygen continuously.

The initiation of the reaction, described above, is optional for a large scale process. Alternatively, the transition metal ion catalysts, an aqueous solution of HBr, and acetic acid can be mixed altogether in the pressure reactor and placed under oxygen without 2-thiophenecarboxaldehyde. After heating, 2-thiophenecarboxaldehyde can be added via the additional funnel to the initial mixture at a desired temperature and under the desired oxygen pressure.

After the oxygen uptake is observed to cease, the cooled reaction mixture is filtered to remove the formed solids. The solvent is removed by evaporation, and the resulting solids are subjected to extraction for isolation of the desired product of 2-thiophenecarboxylic acid.

Alternatively, NaBr is used in the place of HBr in the above-mentioned procedure.

EMBODIMENTS

For further illustration, additional non-limiting embodiments of the present disclosure are set forth below.

For example, embodiment 1 is a process for preparing a heteroaryl carboxylic acid of Formula II:

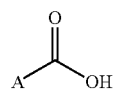

Formula II the process comprising contacting a compound of Formula Ia:

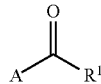

Formula Ia with oxygen in the presence of a catalyst component in an oxidation reaction zone comprising a liquid medium, wherein:
  $R^1$ is $C_1$-$C_6$ alkyl;
  A is a heteroaryl which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, or —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, and $C_1$-$C_4$ alkylamino;
  and wherein the catalyst component comprises a first transition metal ion selected from the group consisting of cobalt, copper, manganese, iron, zinc, zirconium, nickel, palladium, cadmium, and mixtures thereof.

Embodiment 2 is the process of embodiment 1 wherein A is a monocyclic 5-membered heteroaryl or an aryl-fused 5-membered heteroaryl, and the compound of Formula Ia is a compound of Formula Ia-i:

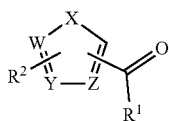

Formula Ia-i wherein:
  X is S, O, NC(O)$OR^b$, or NC(O)$R^b$; $R^b$ is $C_1$-$C_6$ alkyl or aryl;
  W, Y, and Z are each independently selected from the group consisting of N, C, and C(H);
  $R^1$ is $C_1$-$C_6$ alkyl; and
  $R^2$ is one or more of hydrogen, halogen, aryl, $C_1$-$C_4$ alkyl, $C_1$-$C_4$ alkoxy, $C_1$-$C_4$ haloalkyl, $C_1$-$C_4$ haloalkoxy, cyano or —C(O)$R^{21}$, $R^{21}$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; or $R^2$ is aryl, fused to W and Y or Y and Z.

Embodiment 3 is a process for preparing a heteroaryl carboxylic acid of Formula II,

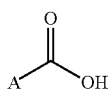

Formula II the process comprising:
  reacting a heteroaromatic compound of Formula A-H with acetic anhydride in the presence of a cation ion exchange resin in an acylating reaction zone to produce a product mixture comprising a compound of Formula Ia-a;

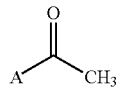

Formula Ia-a and contacting the compound of Formula Ia-a with oxygen in the presence of a catalyst component in a oxidation reaction zone comprising a liquid medium comprising acetic acid and acetic anhydride; wherein:
  A is a heteroaryl which can be optionally independently substituted with one or more substituents selected from the group consisting of hydroxyl, halogen, aryl, $C_1$-$C_4$ alkyl, $C_1$-$C_4$ alkoxy, $C_1$-$C_4$ haloalkyl, $C_1$-$C_4$ haloalkoxy, cyano, and —C(O)$R^a$, wherein $R^a$ is hydrogen, hydroxyl, $C_1$-$C_4$ alkyl, $C_1$-$C_4$ alkoxy, $C_1$-$C_4$ haloalkyl, $C_1$-$C_4$ haloalkoxy, or $C_1$-$C_4$ alkylamino; and
  the catalyst component comprises a first transition metal ion selected from the group consisting of cobalt, copper, manganese, iron, zinc, zirconium, nickel, palladium, cadmium, and mixtures thereof.

Embodiment 4 is the process of embodiment 3 wherein the cation exchange resin is a sulfonic acid-type cation exchange resin selected from the group consisting of a sulfonated styrene-divinyl benzene copolymer, a sulfonated crosslinked styrene polymer, a phenol formaldehyde-sulfonic add resin, and a benzene formaldehyde-sulfonic acid resin.

Embodiment 5 is the process of embodiment 4 wherein the sulfonic acid-type cation exchange resin is DOWEX DR-2030 or AMBERLYST™-15.

Embodiment 6 is the process of any one of embodiments 3 to 5 wherein acetic anhydride is present in the acylating reaction zone in an amount of from about 2 equivalents to about 5 equivalents, from about 2 equivalents to about 4 equivalents, or about 2 equivalents to about 3 equivalents, based on the heteroaromatic compound of Formula A-H.

Embodiment 7 is the process of any one of embodiments 3 to 6 wherein the acylation reaction is carried out at a temperature of from about 20° C. to about 100° C., from about 30° C. to about 80° C., from about 30° C. to about 70° C., from about 30° C. to about 60° C., from about 30° C. to about 50° C., from about 30° C. to about 40° C., from about 40° C. to about 70° C., from about 40° C. to about 60° C., or from about 40° C. to about 50° C.

Embodiment 8 is the process of any one of embodiments 3 to 7 wherein the process further comprises removing the cation exchange resin from the product mixture by filtration.

Embodiment 9 is the process of any one of embodiments 3 to 8 wherein acetic acid is added to the product mixture in an amount of from about 1 equivalent to about 3 equivalents, from about 1 equivalent to about 2 equivalents, or about 1 equivalent, based on the heteroaromatic compound of Formula A-H, thereby forming the liquid medium.

Embodiment 10 is the process of any one of embodiments 3 to 9 wherein A is a monocyclic 5-membered heteroaryl or an aryl-fused 5-membered heteroaryl, and the compound of Formula Ia-a is a compound of Formula Ia-i-a:

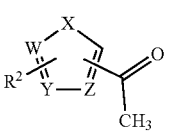

Formula Ia-i-a wherein:

X is S, O, NC(O)OR$^b$, or NC(O)R$^b$; R$^b$ is C$_1$-C$_6$ alkyl or aryl;

W, Y, and Z are each independently selected from the group consisting of N, C, and C(H); and R$^2$ is one or more of hydrogen, halogen, aryl, C$_1$-C$_4$ alkyl, C$_1$-C$_4$ alkoxy, C$_1$-C$_4$ haloalkyl, C$_1$-C$_4$ haloalkoxy, cyano or —C(O)R$^{21}$, R$^{21}$ is hydrogen, hydroxyl, C$_1$-C$_4$ alkyl, C$_1$-C$_4$ alkoxy, C$_1$-C$_4$ haloalkyl, C$_1$-C$_4$ haloalkoxy, or C$_1$-C$_4$ alkylamino; or R$^2$ is aryl, fused to W and Y or Y and Z.

Embodiment 11 is the process of embodiment 2 or embodiment 10 wherein X is S.

Embodiment 12 is the process of embodiment 2 or embodiment 10 wherein X is O.

Embodiment 13 is the process of any one of embodiments 2, or 10 to 12 wherein W, Y, and Z are each C(H).

Embodiment 14 is the process of any one of embodiments 2, or 10 to 12 wherein R$^2$ is phenyl fused to W and Y or Y and Z.

Embodiment 15 is the process of any one of embodiments 1 to 2, or 11 to 14 wherein R$^1$ is CH$_3$.

Embodiment 16 is the process of embodiment 1 wherein the compound of Formula Ia is an acetylthiophene compound of Formula Ia-ii:

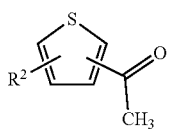

Formula Ia-ii wherein:

R$^2$ is one or more of hydrogen, halogen, aryl, C$_1$-C$_4$ alkyl, C$_1$-C$_4$ alkoxy, C$_1$-C$_4$ haloalkyl, C$_1$-C$_4$ haloalkoxy, cyano or —C(O)R$^{21}$, wherein R$^{21}$ is hydrogen, hydroxyl, C$_1$-C$_4$ alkyl, C$_1$-C$_4$ alkoxy, C$_1$-C$_4$ haloalkyl, C$_1$-C$_4$ haloalkoxy, or C$_1$-C$_4$ alkylamino; or R$^2$ is aryl, fused to the two adjacent carbons of the thiophene ring.

Embodiment 17 is the process of embodiment 16 wherein the compound of Formula Ia-ii is 2-acetylthiophene.

Embodiment 18 is the process of embodiment 17 wherein the process further comprises reacting thiophene with acetic anhydride, thereby producing 2-acetylthiophene.

Embodiment 19 is the process of embodiment 16 wherein the compound of Formula Ia-ii is 3-acetylthiophene.

Embodiment 20 is the process of any one of embodiments 3 to 10 wherein the heteroaromatic compound of Formula A-H is thiophene and the compound of Formula Ia-a is an acetylthiophene compound of Formula Ia-ii:

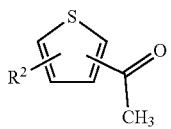

Formula Ia-ii wherein:

R$^2$ is one or more of hydrogen, halogen, aryl, C$_1$-C$_4$ alkyl, C$_1$-C$_4$ alkoxy, C$_1$-C$_4$ haloalkyl, C$_1$-C$_4$ haloalkoxy, cyano or —C(O)R$^{21}$, wherein R$^{21}$ is hydrogen, hydroxyl, C$_1$-C$_4$ alkyl, C$_1$-C$_4$ alkoxy, C$_1$-C$_4$ haloalkyl, C$_1$-C$_4$ haloalkoxy, or C$_1$-C$_4$ alkylamino; or R$^2$ is aryl, fused to the two adjacent carbons of the thiophene ring.

Embodiment 21 is the process of embodiment 20 wherein the compound of Formula Ia-ii is 2-acetylthiophene.

Embodiment 22 is the process of any one of embodiments 1 to 21 wherein the first transition metal ion is selected from the group consisting of manganese, iron, and copper.

Embodiment 23 is the process of embodiment 22 wherein the first transition metal ion is manganese.

Embodiment 24 is the process of any one of embodiments 1 to 23 wherein the catalyst component further comprises a second transition metal ion.

Embodiment 25 is the process of embodiment 24 wherein the second transition metal ion is selected from the group consisting of cobalt, iron, and copper.

Embodiment 26 is the process of embodiment 25 wherein the second transition metal ion is cobalt.

Embodiment 27 is the process of any one of embodiments 1 to 26 wherein the catalyst component comprises cobalt ions and manganese ions.

Embodiment 28 is the process of any one of embodiments 1 to 23 wherein the catalyst component consists of manganese ions.

Embodiment 29 is the process of any one of embodiments 1 to 2, 11 to 19, or 22 to 28 wherein the liquid medium of the oxidation reaction zone further comprises a carboxylic anhydride to assist with the oxidation reaction.

Embodiment 30 is the process of any one of embodiments 1 to 29 wherein the process comprises adding the carboxylic anhydride to the liquid medium prior to or during the contacting step.

Embodiment 31 is the process of embodiment 29 or 30 wherein the carboxylic anhydride is selected from the group consisting of acetic anhydride, acetic propionic anhydride, propionic anhydride, and acetic butyric anhydride.

Embodiment 32 is the process of any one of embodiments 29 to 31 wherein the carboxylic anhydride is present in the liquid medium in an amount of from about 1 equivalent to about 2 equivalents, or from about 1.2 equivalents to about 1.6 equivalents, based on the compound of Formula Ia.

Embodiment 33 is a process for preparing a thiophene carboxylic acid, the process comprising:

contacting a compound of Formula Ib:

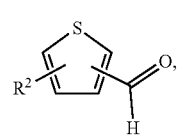

Formula Ib-i with oxygen in the presence of a catalyst component in an oxidation reaction zone comprising a liquid medium, wherein:

R$^2$ is one or more of hydrogen, halogen, aryl, C$_1$-C$_4$ alkyl, C$_1$-C$_4$ alkoxy, C$_1$-C$_4$ haloalkyl, C$_1$-C$_4$ haloalkoxy, cyano or —C(O)R$^{21}$, R$^{21}$ is hydrogen, hydroxyl, C$_1$-C$_4$ alkyl, C$_1$-C$_4$ alkoxy, C$_1$-C$_4$ haloalkyl, C$_1$-C$_4$ haloalkoxy, or C$_1$-C$_4$ alkylamino; or R$^2$ is aryl, fused to the two adjacent carbons of the thiophene ring;

and wherein the catalyst component comprises a first transition metal ion selected from the group consisting of cobalt, copper, manganese, iron, zinc, zirconium, nickel, palladium, cadmium, and mixtures thereof.

Embodiment 34 is the process of embodiment 33 wherein the compound of Formula Ib-i is 2-thiophenecarboxylaldehyde.

Embodiment 35 is the process of embodiment 34 wherein the process further comprises reacting thiophene with N,N-dimethylchloromethyliminium chloride or dimethylformamide in the presence of phosgene or phosphoryl chloride.

Embodiment 36 is the process of embodiment 33 wherein the compound of Formula Ib-i is 3-thiophenecarboxylaldehyde.

Embodiment 37 is the process of any one of embodiments 33 to 36 wherein the first transition metal ion is selected from the group consisting of cobalt, iron, and copper.

Embodiment 38 is the process of embodiment 37 wherein the first transition metal ion is cobalt.

Embodiment 39 is the process of any one of embodiments 33 to 38 wherein the catalyst component further comprises a second transition metal ion.

Embodiment 40 is the process of embodiment 39 wherein the second transition metal ion is selected from the group consisting of manganese, iron, and copper.

Embodiment 41 is the process of embodiment 40 wherein the second transition metal ion is manganese.

Embodiment 42 is the process of any one of embodiments 33 to 41 wherein catalyst component comprises cobalt ions and manganese ions.

Embodiment 43 is the process of any one of embodiments 33 to 38 wherein the catalyst component consists of cobalt ions.

Embodiment 44 is the process of any one of embodiments 1 to 27 or 29 to 42 wherein the ratio of the first transition metal ion to the second transition metal ion is at least about 0.1:1, at least about 1:1, at least about 2:1, at least about 3:1, at least about 4:1, at least about 5:1, at least about 6:1, at least about 7:1, at least about 8:1, at least about 9:1, or at least about 10:1.

Embodiment 45 is the process of any one of embodiments 1 to 27, 29 to 42, or 44 wherein the ratio of the first transition metal ion to the second transition metal ion is from about 0.1:1 to about 100:1, from about 1:1 to about 100:1, from about 1:1 to about 50:1, from about 1:1 to about 40:1, from about 1:1 to about 30:1, from about 1:1 to about 20:1, or from about 3:1 to about 15:1.

Embodiment 46 is the process of any one of embodiments 1 to 2, 11 to 19, or 22 to 45 wherein the liquid medium comprises an alkanoic acid.

Embodiment 47 is the process of any one of embodiments 1 to 46 wherein the first transition metal ion is introduced to the liquid medium in a salt form or a hydrate thereof.

Embodiment 48 is the process of any one of embodiments 1 to 47 wherein the first transition metal ion is introduced to the liquid medium in the salt form of a halide, a $C_2$-$C_6$ alkanoate, a nitrate, a carbonate, or a combination thereof.

Embodiment 49 is the process of embodiment 48 wherein the first transition metal ion is introduced to the liquid medium in the salt form of a $C_2$-$C_6$ alkanoate.

Embodiment 50 is the process of embodiment 49 wherein the first transition metal ion is introduced to the liquid medium in the salt form of an acetate.

Embodiment 51 is the process of any one of embodiments 1 to 50 wherein the second transition metal ion is introduced to the liquid medium in a salt form or a hydrate thereof.

Embodiment 52 is the process of any one of embodiments 1 to 27, 29 to 42, or 44 to 51 wherein the second transition metal ion is introduced to the liquid medium in the salt form of a halide, a $C_2$-$C_6$ alkanoate, a nitrate, a carbonate, or a combination thereof.

Embodiment 53 is the process of embodiment 52 wherein the second transition metal ion is introduced to the liquid medium in the salt form of a $C_2$-$C_6$ alkanoate.

Embodiment 54 is the process of embodiment 53 wherein the second transition metal ion is introduced to the liquid medium in the salt form of an acetate.

Embodiment 55 is the process of embodiment 49 wherein the anion of the first transition metal salt is predominately the same as the anion of the alkanoic acid.

Embodiment 56 is the process of embodiment 53 wherein the anion of the second transition metal salt is predominately the same as the anion of the alkanoic acid.

Embodiment 57 is the process of any one of embodiments 1 to 56 wherein the liquid medium or the alkanoic acid comprises acetic acid, the liquid medium comprises the first transition metal ion introduced predominately in the salt form of an acetate, and the liquid medium comprises the second transition metal ion introduced predominately in the salt form of an acetate.

Embodiment 58 is the process of any one of embodiments 1 to 57 wherein the first transition metal ion is present in the liquid medium in an amount of 0.01 mol % to about 5 mol %, from about 0.1 mol % to about 5 mol %, from about 0.5 mol % to about 5 mol %, or from about 1 mol % to about 5 mol %, based on the compound of Formula Ia or the compound of Formula Ib.

Embodiment 59 is the process of any one of embodiments 1 to 27, 29 to 42, or 44 to 58 wherein the second transition metal ion is present in the liquid medium in an amount of from about 0.01 mol % to about 5 mol %, from about 0.1 mol % to about 1 mol %, or from about 0.1 mol % to about 0.5 mol %, based on the compound of Formula Ia or the compound of Formula Ib.

Embodiment 60 is the process of any one of embodiments 1 to 59 wherein the process comprises adding nitric acid to the liquid medium prior to or during the contacting step to assist with the oxidation reaction.

Embodiment 61 is the process of embodiment 60 wherein nitric acid is present in the liquid medium in an amount of 0.01 mol % to about 10 mol %, based on the compound of Formula Ia or the compound of Formula Ib.

Embodiment 62 is the process of any one of embodiments 1 to 61 wherein the process comprises adding a nitrate salt to the liquid medium prior to or during the contacting step to assist with the oxidation reaction.

Embodiment 63 is the process of embodiment 62 wherein the nitrate salt comprises alkaline or alkaline earth metal nitrate.

Embodiment 64 is the process of embodiment 63 wherein the alkaline or alkaline earth metal is selected from the group consisting of K, Na, Ce, and Ca.

Embodiment 65 is the process of embodiment 64 wherein the nitrate salt comprises sodium nitrate.

Embodiment 66 is the process of any one of embodiments 62 to 65 wherein the nitrate salt is present in the liquid medium in an amount of 0.01 mol % to about 10 mol %, based on the compound of Formula Ia or the compound of Formula Ib.

Embodiment 67 is the process of one of embodiments 1 to 66 wherein the process comprises adding a co-reductant to the liquid medium during the contacting step to assist with the oxidation reaction.

Embodiment 68 is the process of embodiment 67 wherein the co-reductant comprises $C_2$-$C_4$ alkyl aldehyde or $C_1$-$C_4$ dialkyl ketone.

Embodiment 69 is the process of embodiment 67 or 68 wherein the co-reductant is present in the liquid medium in an amount of 0.01 mol % to about 30 mol %, based on the compound of Formula Ia or the compound of Formula Ib.

Embodiment 70 is the process of any one of embodiments 1 to 69 wherein the liquid medium comprises a source of halide ions to assist with the oxidation reaction.

Embodiment 71 is the process of embodiment 70 wherein the process comprises adding a hydrohalic acid to the liquid medium prior to or during the contacting step.

Embodiment 72 is the process of embodiment 71 wherein the hydrohalic acid comprises hydrogen bromide or hydrogen chloride.

Embodiment 72 is the process of embodiment 70 wherein the process comprises adding a halide salt to the liquid medium prior to or during the contacting step.

Embodiment 74 is the process of embodiment 73 wherein the halide salt comprises alkaline or alkaline earth metal bromide or chloride.

Embodiment 75 is the process of embodiment 74 wherein the alkaline or alkaline earth metal is selected from the group consisting of K, Na, Ce, and Ca Embodiment 76 is the process of any one of embodiments 73 to 75 wherein the halide salt is selected from the group consisting of sodium bromide, sodium chloride, and potassium chloride.

Embodiment 77 is the process of any one of embodiments 70 to 76, wherein the halide ion is present in the liquid medium in an amount of 0.1 mol % to about 10 mol %, from about 1 mol % to about 5 mol %, or from about 2 mol % to about 5 mol %, based on the compound of Formula Ia or the compound of Formula Ib.

Embodiment 78 is the process of any one of embodiments 70 to 77 wherein the halide ion comprises bromide, the liquid medium further comprises a zinc (II) salt to assist with the oxidation reaction.

Embodiment 79 is the process of embodiment 78 wherein the process comprises adding a zinc (II) salt to the liquid medium prior to or during the contacting step.

Embodiment 80 is the process of embodiment 79 wherein the zinc (II) salt comprises zinc acetate.

Embodiment 81 is the process of any one of embodiments 78 to 80, wherein the zinc (II) salt is present in the liquid medium in an amount of 0.1 mol % to about 10 mol %, from about 1 mol % to about 5 mol %, or from about 2 mol % to about 5 mol %, based on the compound of Formula Ia or the compound of Formula Ib.

Embodiment 82 is the process of any one of embodiments 1 to 72 wherein the first transition metal ion and the second transition metal ion are optionally generated from the transition metals in the liquid medium comprising a hydrohalic acid.

Embodiment 83 is the process of any one of embodiments 1 to 2, 11 to 19, or 22 to 82 wherein the alkanoic acid comprises a $C_2$-$C_6$ linear or branched carboxylic acid.

Embodiment 84 is the process of embodiment 83 wherein the alkanoic acid comprises acetic acid.

Embodiment 85 is the process of any one of embodiments 1 to 84 wherein the source of oxygen in the reaction zone is substantially pure oxygen.

Embodiment 86 is the process of any one of embodiments 1 to 85 wherein the source of oxygen is air.

Embodiment 87 is the process of any one of embodiments 1 to 86 wherein the partial pressure of oxygen in the oxidation reaction zone is from about 1 atm to about 50 atm, from about 1 atm to about 40 atm, from about 1 atm to about 30 atm, from about 1 atm to about 20 atm, or from about 1 atm to about 10 atm.

Embodiment 88 is the process of any one of embodiments 1 to 87 wherein oxygen is periodically introduced into the oxidation reaction zone, and the head space above the liquid medium in a reactor defining the oxidation reaction zone is periodically purged.

Embodiment 89 is the process of any one of embodiments 1 to 88 wherein oxygen is continuously introduced into the oxidation reaction zone.

Embodiment 90 is the process of embodiment 89 wherein the head space above the liquid medium in a reactor defining the oxidation reaction zone is continuously purged at the rate that an initial partial pressure of oxygen is maintained in the oxidation zone.

Embodiment 91 is the process of any one of embodiments 1 to 90 wherein the contacting step is carried out at a temperature from about 70° C. to about 150° C., from about 80° C. to about 140° C., from about 90° C. to about 130° C., from about 100° C. to about 120° C., or from about 110° C. to about 120° C.

Embodiment 92 is the process of any one of embodiments 1 to 91 wherein the process further comprises an extraction step in which the heteroaryl carboxylic acid of Formula II is extracted with an extraction liquid medium comprising an organic solvent.

Embodiment 93 is the process of embodiment 92 wherein the organic solvent in the extraction step forms an azeotrope with water.

Embodiment 94 is a process for preparing a heteroaryl acyl chloride of Formula III

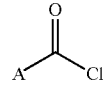

Formula III wherein A is an optionally independently substituted heteroaryl, the process comprising chlorinating the heteroaryl carboxylic acid of Formula II prepared in any one of embodiments 1 to 93 by reacting a chlorinating agent with the heteroaryl carboxylic acid dissolved in a chlorination medium comprising an organic solvent.

Embodiment 95 is the process of embodiment 94 wherein the chlorinating agent comprises thionyl chloride.

Embodiment 96 is the process of embodiment 95 wherein the heteroaryl carboxylic acid of Formula II is 2-thiophenecarboxylic acid and the heteroaryl acyl chloride of Formula III is 2-thiophenecarbonyl chloride.

Embodiment 97 is the process of any one of embodiments 92 to 96 wherein the organic solvent in the extraction step and the organic solvent in the chlorinating step are the same.

Embodiment 98 is a process for preparing a 3,5-disubstituted 1,2,4-oxadiazole of Formula IV or a salt thereof,

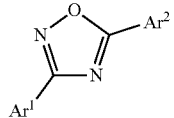

Formula IV wherein $Ar^1$ is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, the process comprising reacting an N-hydroxyamidine of Formula V, or a tautomeric form thereof,

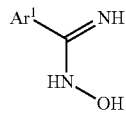

Formula V with 2-thiophenecarbonyl chloride prepared by a process as set forth in any one of embodiments 94 to 97.

Embodiment 99 is a process for preparing a 3,5-disubstituted 1,2,4-oxadiazole of Formula IV or a salt thereof,

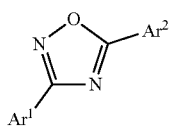

Formula IV wherein $Ar^1$ is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, the process comprising reacting thiophene with acetic anhydride in an acylation reaction medium comprising a mineral acid or a cation exchange, thereby producing 2-acetylthiophene;

contacting 2-acetylthiophene with a oxygen in an oxidation reaction zone comprising a liquid medium comprising an alkanoic acid, thereby producing 2-thiophenecarboxylic acid;

reacting 2-thiophenecarboxylic acid dissolved in a chlorination medium comprising an organic solvent with thionyl chloride, thereby producing 2-thiophenecarboynl chloride;

and reacting 2-thiophenecarbonyl chloride with an N-hydroxyamidine of Formula V, or a tautomeric form thereof,

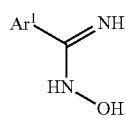

Formula V thereby producing a 3,5-disubstituted 1,2,4-oxadiazole or a salt thereof.

Embodiment 100 is the process of embodiment 99 wherein the acylation is carried out in the presence of the cation exchange resin to produce a product mixture comprising 2-acetylthiophene, acetic acid, and acetic anhydride; and wherein the process further comprises removing the cation exchange resin from the product mixture; modifying the product mixture with acetic acid to form the liquid medium; and transferring the liquid medium to the oxidation reaction zone.

Embodiment 101 is a process for preparing a 3,5-disubstituted 1,2,4-oxadiazole of Formula IV or a salt thereof,

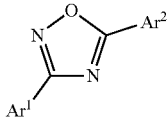

Formula IV wherein $Ar^1$ is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl, the process comprising reacting thiophene with dimethylformamide in the presence of phosgene or phosphoryl chloride in a reaction medium comprising an organic solvent, thereby producing 2-thiophenecarboxaldehyde;

contacting 2-thiophenecarboxyaldehyde with oxygen in an oxidation reaction zone comprising a liquid medium comprising an alkanoic acid, thereby producing 2-thiophenecarboxylic acid;

reacting 2-thiophenecarboxylic acid dissolved in a chlorination medium comprising an organic solvent with thionyl chloride, thereby producing 2-thiophenecarbonyl chloride;

and reacting 2-thiophenecarbonyl chloride with an N-hydroxyamidine of Formula V, or a tautomeric form thereof,

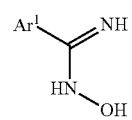

Formula V thereby producing a 3,5-disubstituted 1,2,4-oxadiazole or a salt thereof.

Embodiment 102 is the process of any one of embodiments 98 to 101 wherein the 3,5-disubstituted-1,2,4-oxadiazole of Formula IV is 3-phenyl-5-(2-thienyl)-1,2,4-oxadiazole, or a salt thereof.

When introducing elements of the present disclosure or the preferred embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A process for preparing 2-thiophenecarboxylic acid or 3-thiophenecarboxylic acid the process comprising contacting 2-acetylthiophene or 3-acetylthiophene with oxygen in the presence of a catalyst component in an oxidation reaction zone comprising a liquid medium, comprising an alkanoic acid, wherein the catalyst component comprises a first transition metal ion selected from the group consisting of cobalt, copper, manganese, iron, zinc, zirconium, nickel, palladium, cadmium, and mixtures thereof.

2. The process of claim 1 further comprising:
reacting thiophene with acetic anhydride in the presence of a cation ion exchange resin in an acylating reaction zone to produce a product mixture comprising 2-acetylthiophene or 3-acetylthiophene.

3. The process of claim 1 wherein the first transition metal ion is selected from the group consisting of manganese, iron, and copper.

4. The process of claim 3 wherein the first transition metal ion is manganese.

5. The process of claim 1 wherein the catalyst component further comprises a second transition metal ion.

6. The process of claim 5 wherein the second transition metal ion is selected from the group consisting of cobalt, iron, and copper.

7. The process of claim 1 wherein the first transition metal ion is introduced to the liquid medium in a salt form of a halide, a $C_2$-$C_6$ alkanoate, a nitrate, a carbonate, or a combination thereof.

8. The process of claim 1 wherein the process comprises adding a nitrate salt to the liquid medium prior to or during the contacting step to assist with the oxidation reaction.

9. The process of claim 1 wherein the liquid medium comprises a source of halide ions to assist with the oxidation reaction.

10. The process of claim 1 wherein the process further comprises an extraction step in which 2-thiophenecarboxylic acid or 3-thiophenecarboxylic acid is extracted with an extraction liquid medium comprising an organic solvent, and wherein the organic solvent in the extraction step forms an azeotrope with water.

11. The process of claim 1 further comprising chlorinating the thiophene carboxylic acid by reacting a chlorinating agent with the thiophene carboxylic acid dissolved in a chlorination medium comprising an organic solvent to produce thiophene carbonyl chloride.

12. The process of claim 11 further comprising reacting an N-hydroxyamidine of Formula V, or a tautomeric form thereof,

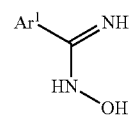

Formula V with the thiophene carbonyl chloride, wherein the thiophene carbonyl chloride is 2-thiophenecarbonyl chloride, to produce a 3,5-disubstituted 1,2,4-oxadiazole of Formula IV or a salt thereof:

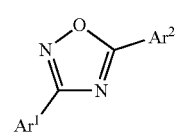

Formula IV wherein $Ar^1$ is selected from the group consisting of phenyl, pyridyl, pyrazyl, oxazolyl, and isoxazolyl, each of which can be optionally independently substituted with one or more substituents selected from the group consisting of halogen, $CF_3$, $CH_3$, $OCF_3$, $OCH_3$, CN and C(H)O, and $Ar^2$ is thienyl.

13. The process of claim 1 wherein the source of oxygen is air.

14. The process of claim 6 wherein the second transition metal ion is cobalt.

15. The process of claim 1 wherein the alkanoic acid is selected from the group consisting of acetic acid and propionic acid.

16. The process of claim 9 wherein the source of halide ions is selected from the group consisting of hydrohalic acids and halide salts.

17. The process of claim 16 wherein the source of halide ions is selected from the group consisting of sodium bromide, sodium chloride, and hydrobromic acid.

18. The process of claim 16 wherein the source of halide ions is a halide salt.

19. The process of claim 18 wherein the halide salt is a calcium salt, a cesium salt, a lithium salt, a sodium salt, or a potassium salt.

* * * * *